(12) United States Patent
Bouchard et al.

(10) Patent No.: US 6,995,175 B2
(45) Date of Patent: Feb. 7, 2006

(54) CHEMICAL DERIVATIVES AND THEIR APPLICATION AS ANTITELOMERASE AGENT

(75) Inventors: Hervé Bouchard, Thiais (FR); Augustin Hittinger, Igny (FR)

(73) Assignee: Aventis Pharma S.A., Antony (FR)

( * ) Notice: Subject to any disclaimer, the term of this patent is extended or adjusted under 35 U.S.C. 154(b) by 30 days.

(21) Appl. No.: 10/721,210

(22) Filed: Nov. 25, 2003

(65) Prior Publication Data

US 2004/0138257 A1    Jul. 15, 2004

Related U.S. Application Data

(63) Continuation of application No. PCT/FR02/01767, filed on May 27, 2002.

(30) Foreign Application Priority Data

May 28, 2001  (FR) .................................. 01 06909
Feb. 4, 2002  (FR) .................................. 02 01256

(51) Int. Cl.
C07D 401/02    (2006.01)
A61K 31/44     (2006.01)
A61K 31/47     (2006.01)

(52) U.S. Cl. ...................... 514/314; 514/256; 514/311; 514/332; 514/333; 544/333; 546/162; 546/255; 546/256

(58) Field of Classification Search ................ 546/162, 546/255, 256; 514/311, 314, 332, 333, 256; 544/333

See application file for complete search history.

(56) References Cited

U.S. PATENT DOCUMENTS

| 5,767,278 A | 6/1998 | Gaeta et al. |
| 5,863,936 A | 1/1999 | Gaeta et al. |
| 6,362,210 B1 | 3/2002 | Hauel et al. |

FOREIGN PATENT DOCUMENTS

| DE | 19935219 | | 2/2001 |
| EP | 1147295 | * | 4/1969 |
| WO | WO 01/07020 | | 2/2001 |
| WO | WO 01/40218 | | 6/2001 |
| WO | WO 02/076975 | | 10/2002 |

OTHER PUBLICATIONS

Hiratani et al, Bulletin of the Chemical Society of Japan, vol. 63, No. 11, pp. 3331-3333, 1990.*
Denny et al, Journal of Medicinal Chemistry, vol. 22, No. 2, pp. 134-150, 1979.*

* cited by examiner

*Primary Examiner*—Zinna Northington Davis
(74) *Attorney, Agent, or Firm*—Balaram Gupta

(57) ABSTRACT

The present invention relates to cancer therapy and to novel anticancer agents having a mechanism of action which is quite specific. It also relates to novel chemical compounds as well as their therapeutic application in humans.

29 Claims, No Drawings

CHEMICAL DERIVATIVES AND THEIR APPLICATION AS ANTITELOMERASE AGENT

This application is a continuation of International application No. PCT/FR02/01,767, filed May 27, 2002; which claims the benefit of priority of French Patent Application No. 01/06,909, filed May 28, 2001 and French Patent Application No. 02/01,256, filed Feb. 4, 2002.

The present invention relates to cancer therapy and to novel anticancer agents having a mechanism of action which is quite specific. It also relates to novel chemical compounds as well as their therapeutic application in humans.

The present invention relates to the use of novel non-nucleotide chemical compounds which interact with specific structures of deoxyribonucleic acid (DNA) or ribonucleic acid (RNA). These novel compounds consist of a distribution agent linked to two aminoaromatic groups. These novel compounds are useful in the treatment of cancers and act in particular as telomerase-inhibiting agents. They are particularly useful for stabilizing DNA in G-quadruplex structure (guanine tetrads). The therapeutic application of the inhibition of telomerase via the stabilization of these G-quadruplexes is the termination of cellular mitosis and the death of rapidly-dividing cells such as cancer cells and possibly the induction of the senescence of cancer cells.

The compounds of the present invention have the advantage, from the therapeutic point of view, of blocking telomerase. From a biological point of view, telomerase allows the addition of repetitive DNA sequences of the T T A G G G type, termed telomeric sequences, at the end of the telomere, during cell division. Through this action, telomerase renders the cell immortal. Indeed, in the absence of this enzymatic activity, the cell loses, at each division, 100 to 150 bases, which rapidly renders it senescent. During the appearance of rapidly-dividing cancer cells, it appeared that these cells possessed telomeres which were maintained at a stable length during cell division. In these cancer cells, it appeared that telomerase was highly activated and that it allowed the addition of repetitive motifs of telomeric sequences at the end of the telomere and therefore allowed conservation of the length of the telomere in the cancer cells. It appeared during the past few years that more than 85% of cancer cells showed positive tests for the presence of telomerase whereas somatic cells do not show this characteristic.

Thus, telomerase is a highly coveted target for treating cancer cells. The first obvious approach for blocking telomerase was the use of nucleotide structures (Chen and al., Proc. Natl. Acad. Sci. USA 93(7), 2635–2639). Among the non-nucleotide compounds which have been used in the prior art, there may be mentioned the diaminoanthraquinones (Sun and al., J. Med. Chem. 40(14), 2113–6) or the diethyloxadicarbocyanins (Wheelhouse R. T. et al., J. Am. Chem. Soc. 1998(120) 3261–2).

WO 99/40087 describes the use of compounds which interact with the G-quadruplex structures which are perylene compounds and carbocyanins containing at least seven rings including two heterocycles.

It appeared, quite surprisingly, that simple structures made it possible to obtain a result which is at least equivalent with structures which are a lot less complicated from a chemical point of view. The compounds of the present invention which meet the intended objective, that is to say which bind the G-quadruplex structure of DNA or of RNA and in particular the G-quadruplex structure of telomeres and thereby exhibit a telomerase-inhibiting activity, correspond to the following general formula (1A):

nitrogen-containing aromatic ring —$(NR_3)p$-$(CO)n$-distribution agent —$(CO)m$- $(NR'_{13})q$- aromatic or non-aromatic ring with n, m, p and q, which are identical or different, representing the integer 0 or 1,
in which
the nitrogen-containing aromatic ring represents:
  a quinoline optionally substituted with at least
    one group N(Ra)(Rb) in which Ra and Rb, which are identical or different, represent hydrogen or a C1–C4 alkyl radical or
    one short-chain C1–C4 alkyl or alkoxy group or
  a quinoline possessing a nitrogen atom in quaternary form or
  a benzamidine or
  a pyridine
the aromatic or non-aromatic ring represents
  a quinoline optionally substituted with at least
    one group N(Ra)(Rb) in which Ra and Rb, which are identical or different, represent hydrogen or a C1–C4 alkyl radical or
    one short-chain C1–C4 alkyl or alkoxy group or
  a quinoline possessing a nitrogen atom in quaternary form or
  a benzamidine or
  a pyridine or
  a phenyl nucleus optionally substituted with a halogen atom, a C1–C4 alkoxy group, a cyano group, a carbonylamino group optionally substituted with one or more C1–C4 alkyl groups, a guanyl group, a C1–C4 alkylthio group, an amino group, a C1–C4 alkylamino group, a C1–C4 dialkylamino group for each alkyl group, a nitro group, a C1–C4 alkyleneamino group or a C2–C4 alkenyleneamino group or
  a mono- or bi- or tricyclic aromatic or non-aromatic heterocyclic nucleus containing 0 to 2 heteroatoms per ring provided that at least one heteroatom is present in at least one ring optionally substituted with one or more C1–C4 alkyl groups or with C1–C4 alkylene or C2–C4 alkenylene groups $R_3$ and $R'_3$, which are identical or different, represent independently of each other hydrogen or a C1–C4 alkyl radical the distribution agent represents:
  a triazine group optionally substituted with one or more radicals chosen from halogen atoms, alkyl radicals having 1 to 4 carbon atoms and thio, oxy or amino radicals which are themselves optionally substituted with one or more short-chain alkyl chains containing 1 to 4 carbon atoms or
  a 5- or 6-membered heterocyclic radical containing a sulfur, oxygen or nitrogen atom
  a phenyl, —NH-phenyl-NH—, —NH-phenyl-CH2-NH—, —NH-CH2-phenyl-CH2-NH—, —NH-CH2-phenyl-NH—, —CH2-phenyl-CH2—, —CH2-phenyl, -phenyl-CH2—, —CH2-thienyl-, -thienyl-CH2—, or —CH=CH— radical, or
  a diazine group, and wherein the heterocyclic, phenyl, —NH-phenyl-NH—, —NH-phenyl-CH2-NH—, —NH—CH2-phenyl-CH2-NH—, —NH—CH2-phenyl-NH—, —CH2-phenyl-CH2—, —CH2-phenyl, -phenyl-CH2—, —CH2-thienyl-, -thienyl-CH2—, or —CH=CH— radical, and diazine radicals being optionally substituted with the same groups as the triazine it being understood that when the distribution agent represents phenyl optionally substituted with $NH_2$, and when n, m, p and q represent 1 and $R_3$ and $R'_3$ represent hydrogen, then the nitrogen-containing aromatic ring and the aromatic ring do not both represent a quinoline which is unsubstituted or substituted on its nitrogen atom with an alkyl radical containing 1 to 6 carbon atoms, or one of its salts and when the distribution agent represents a triazine and p and q both represent the integer 1, then n and m do not both represent the integer 0.

The subject of the present invention is thus in particular the products which correspond to the following general formula:

nitrogen-containing aromatic ring —$NR_3$—(CO)n-distribution agent —(CO)m-$NR'_3$- aromatic or non-aromatic ring with n and m which are identical or different, representing the integer 0 or 1,
in which
the nitrogen-containing aromatic ring represents:
a quinoline optionally substituted with at least one group N(Ra)(Rb) in which Ra and Rb, which are identical or different, represent hydrogen or a C1–C4 alkyl radical or
one short-chain C1–C4 alkyl or alkoxy group or
a quinoline possessing a nitrogen atom in quaternary form or
a benzamidine or
a pyridine
the aromatic or non-aromatic ring represents
a quinoline optionally substituted with at least one group N(Ra)(Rb) in which Ra and Rb, which are identical or different, represent hydrogen or a C1–C4 alkyl radical or
one short-chain C1–C4 alkyl or alkoxy group or
a quinoline possessing a nitrogen atom in quaternary form or
a benzamidine or
a pyridine or
a phenyl nucleus optionally substituted with a halogen atom, a C1–C4 alkoxy group, a cyano group, a carbonylamino group optionally substituted with one or more C1–C4 alkyl groups, a guanyl group, a C1–C4 alkylthio group, an amino group, a C1–C4 alkylamino group, a C1–C4 dialkylamino group for each alkyl group, a nitro group, a C1–C4 alkyleneamino group or a C2–C4 alkenyleneamino group or
a mono- or bi- or tricyclic aromatic or non-aromatic heterocyclic nucleus containing 0 to 2 heteroatoms per ring provided that at least one heteroatom is present in at least one ring optionally substituted with one or more C1–C4 alkyl groups or with C1–C4 alkylene or C2–C4 alkenylene groups
$R_3$ and $R'_3$, which are identical or different, represent independently of each other hydrogen or a C1–C4 alkyl radical
the distribution agent represents:
a triazine group optionally substituted with one or more radicals chosen from halogen atoms, alkyl radicals having 1 to 4 carbon atoms and thio, oxy or amino radicals which are themselves optionally substituted with one or more short-chain alkyl chains containing 1 to 4 carbon atoms or
a 5- or 6-membered heterocyclic radical containing a sulfur, oxygen or nitrogen atom a phenyl, —NH-phenyl-NH—, —NH-phenyl-CH2-NH— or —NH—CH2-phenyl-CH2-NH— radical or
a diazine group, and wherein
the heterocyclic, phenyl, —NH-phenyl-NH, —NH-phenyl-CH2-NH— or —NH—CH2-phenyl-CH2-NH— radicals, and diazine radicals being optionally substituted with the same groups as the triazine it being understood that when the distribution agent represents phenyl optionally substituted with $NH_2$, that n and m represent 1 and $R_3$ and $R'_3$ represent hydrogen, then the nitrogen-containing aromatic ring and the aromatic ring do not both represent a quinoline which is unsubstituted or substituted on its nitrogen atom with an alkyl radical containing 1 to 6 carbon atoms, or one of its salts.

Within the meaning of the above formula, the expression nitrogen-containing aromatic ring is understood to mean a heterocycle containing at least one nitrogen atom or an aromatic group not containing a heteroatom in the ring but containing at least one nitrogen atom in a hydrocarbon chain linked to the ring such as, for example, a guanidino or guanyl chain.

The present invention relates in particular to the above compounds, characterized in that the distribution agent is chosen from the heterocyclic groups, the phenyl, —NH-phenyl-NH—, —NH-phenyl-CH2-NH—, —NH—CH2-phenyl-CH2-NH—, —NH—CH2-phenyl-NH—, —CH2-phenyl-CH2—, —CH2-phenyl, -phenyl-CH2—, —CH2-thienyl-, -thienyl-CH2—, —CH=CH— and diazine radicals, more particularly from the heterocyclic groups, the phenyl, —NH-phenyl-NH—, —NH-phenyl-CH2-NH—, —NH—CH2-phenyl-CH2-NH—, —CH2-phenyl-CH2—, —CH2-phenyl, —CH2-thienyl-, —CH=CH— and diazine radicals, and still more particularly from the heterocyclic groups, the phenyl, —NH-phenyl-NH—, —NH-phenyl-CH 2-NH—, —NH—CH2-phenyl-CH2-NH—, —CH2-phenyl-CH2—, —CH=CH—, and diazine radicals as defined above.

Among all the compounds above, those preferred contain a distribution agent chosen from the heterocyclic groups such as for example thienyl and pyridyl, a phenyl, —NH-phenyl-NH—, —NH-phenyl-CH2-NH—, —NH—CH2-phenyl-CH2-NH— and diazine radical as defined above and which are optionally substituted as indicated above. Among the diazine groups, the use of pyrimidines is preferred.

Among the compounds of the present invention, the compounds defined above, characterized in that p and q represent the integer 1, are especially preferred.

The present invention relates particularly to the compounds defined above, characterized in that they correspond to formula (IA) below:

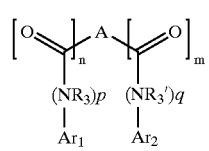

(IA)

with n, m, p and q, which are identical or different, representing the integer 0 or 1 and in which:

A represents:
- a 5- to 6-membered heterocyclic radical containing a sulfur, oxygen or nitrogen atom,
- a phenyl, —NH-phenyl-NH—, —NH-phenyl-CH2-NH—, —NH—CH2-phenyl-CH2-NH—, —NH—CH2-phenyl-NH—, —CH2-phenyl-CH2—, —CH2-phenyl, -phenyl-CH2—, —CH2-thienyl-, -thienyl-CH2— or —CH═CH-radical, or
- a diazine group, and wherein the heterocyclic, phenyl, —NH-phenyl-NH—, —NH-phenyl-CH2-NH—, —NH—CH2-phenyl-CH2-NH—, —NH—CH2-phenyl-NH—, —CH2-phenyl-CH2—, —CH2-phenyl, -phenyl-CH2—, —CH2-thienyl-, -thienyl-CH2— or —CH═CH— radical, and diazine radicals which A may represent, are optionally substituted with one or more radicals chosen from halogen atoms, alkyl radicals having 1 to 4 carbon atoms and thio, oxy or amino radicals which are themselves optionally substituted with one or more short-chain alkyl chains containing 1 to 4 carbon atoms, $R_3$ and $R'_3$, which are identical or different, represent independently of each other hydrogen or a C1–C4 alkyl group $Ar_1$ and $Ar_2$, which are identical or different, represent when $Ar_1$ and $Ar_2$ are identical:
- a quinoline unit optionally substituted with at least
  - a group N(Ra)(Rb) in which Ra and Rb, which are identical or different, represent hydrogen or a C1–C4 alkyl radical or
  - a short-chain alkyl or alkoxy group containing 1 to 4 carbon atoms or
- a quinoline possessing a nitrogen atom in quaternary form or
- a benzamidine or
- a pyridine attached at the 4-position or fused with an aryl or heteroaryl group, optionally substituted with a C1–C4 alkyl group when $Ar_1$ and $Ar_2$ are different $Ar_1$ and $Ar_2$ both represent one of the possibilities mentioned above for $Ar_1$ and $Ar_2$ or $Ar_1$ represents one of the above possibilities and $Ar_2$ represents
- a phenyl nucleus optionally substituted with a halogen atom, a C1–C4 alkoxy group, a cyano group, a carbonylamino group optionally substituted with one or more C1–C4 alkyl groups, a guanyl group, a C1–C4 alkylthio group, an amino group, a C1–C4 alkylamino group, a C1–C4 dialkylamino group for each alkyl group, a nitro group, a C1–C4 alkyleneamino group or a C2–C4 alkyleneamino group
- a pyridyl nucleus
- a mono- or bi- or tricyclic aromatic or non-aromatic heterocyclic nucleus containing 0 to 2 heteroatoms per ring provided that at least one heteroatom is present in at least one ring optionally substituted with one or more C1–C4 alkyl groups or with C1–C4 alkylene or C2–C4 alkenylene groups, it being understood that when A represents a phenyl optionally substituted with NH2 and when n, m, p and q represent 1 and $R_3$ and $R_3'$ represent hydrogen, then the nitrogen-containing aromatic ring and the aromatic ring do not both represent a quinoline which is unsubstituted or substituted on its nitrogen atom with an alkyl radical containing 1 to 6 carbon atoms or one of its salts and when A represents a triazine and p and q both represent the integer 1, then n and m do not both represent the integer 0.

The present invention relates in particular to the above compounds, characterized in that A is chosen from the heterocyclic groups, the phenyl, —NH-phenyl-NH—, —NH-phenyl-CH2-NH—, —NH—CH2-phenyl-CH2-NH—, —NH—CH2-phenyl-NH—, —CH2-phenyl-CH2—, —CH2-phenyl, -phenyl-CH2—, —CH2-thienyl-, -thienyl-CH2—, —CH═CH— and diazine radicals, more particularly from the heterocyclic groups, the phenyl, —NH-phenyl-NH—, —NH-phenyl-CH2-NH—, —NH—CH2-phenyl-CH2-NH—, —CH2-phenyl-CH2—, —CH2-phenyl, —CH2-thienyl-, —CH═CH— and diazine radicals, and still more particularly from the heterocyclic groups, the phenyl, —NH-phenyl-NH—, —NH-phenyl-CH2-NH—, —NH—CH2-phenyl-CH2-NH—, —CH2-phenyl-CH2—, —CH═CH—, and diazine radicals as defined above.

Among the compounds of the present invention, those preferred are in particular the compounds corresponding to formula (I) below:

$$\left[O=\right]_n A \left[=O\right]_m \quad (I)$$
$$\underset{Ar_1}{NR_3} \quad \underset{Ar_2}{NR_3'}$$

with n and m, which are identical or different, representing the integer 0 or 1 and in which:

A represents:
- a 5- to 6-membered heterocyclic radical containing a sulfur, oxygen or nitrogen atom,
- a phenyl, —NH-phenyl-NH—, —NH-phenyl-CH2-NH— or —NH—CH2-phenyl-CH2-NH— radical, or
- a diazine group, and wherein the heterocyclic, phenyl, —NH-phenyl-NH—, —NH-phenyl-CH2-NH—, —NH—CH2-phenyl-CH2-NH— and diazine radicals which A may represent, are optionally substituted with one or more radicals chosen from halogen atoms, alkyl radicals having 1 to 4 carbon atoms and thio, oxy or amino radicals which are themselves optionally substituted with one or more short-chain alkyl chains containing 1 to 4 carbon atoms, $R_3$ and $R'_3$, which are identical or different, represent independently of each other hydrogen or a C1–C4 alkyl group, $Ar_1$ and $Ar_2$, which are identical or different, represent
1. when $Ar_1$ and $Ar_2$ are identical:
   - a quinoline unit optionally substituted with at least
     - a group N(Ra)(Rb) in which Ra and Rb, which are identical or different, represent hydrogen or a C1–C4 alkyl radical or
     - a short-chain alkyl or alkoxy group containing 1 to 4 carbon atoms or
   - a quinoline possessing a nitrogen atom in quaternary form or
   - a benzamidine or
   - a pyridine attached at the 4-position or fused with an aryl or heteroaryl group, optionally substituted with a C1–C4 alkyl group
2. when $Ar_1$ and $Ar_2$ are different
   $Ar_1$ and $Ar_2$ both represent one of the possibilities mentioned above for $Ar_1$ and $Ar_2$ or Ar₁ represents one of the above possibilities and Ar₂ represents
- a phenyl nucleus optionally substituted with a halogen atom, a C1–C4 alkoxy group, a cyano group, a carbonylamino group optionally substituted with one or more C1–C4 alkyl groups, a guanyl group, a C1–C4 alkylthio group, an amino group, a C1–C4 alkylamino group, a C1–C4 dialkylamino group for each alkyl group, a nitro group, a C1–C4 alkyleneamino group or a C2–C4 alkenyleneamino group
- a pyridyl nucleus
- a mono- or bi- or tricyclic aromatic or non-aromatic heterocyclic nucleus containing 0 to 2 heteroatoms per ring provided that at least one heteroatom is present in at least one ring optionally substituted with one or more C1–C4 alkyl groups or with C1–C4 alkylene or C2–C4 alkenylene groups, it being understood that when A represents a phenyl optionally substituted with NH2 and when n and m represent 1 and R₃ and R₃' represent hydrogen, then the nitrogen-containing aromatic ring and the aromatic ring do not both represent a quinoline which is unsubstituted or substituted on its nitrogen atom with an alkyl radical containing 1 to 6 carbon atoms or one of its salts.

It is evident that quinoline units may be substituted with any other group not involved in the desired application; thus, acridine or isoquinoline or quinazoline or quinoxaline or phthalazine or benzothiazine or benzoxazine or phenoxazine or phenothiazine groups are included in the definition of quinoline groups.

In the above compounds, the diazine groups which A may represent are preferably pyrimidines.

Among the compounds of formula (I) above, those preferred are the ones for which A is chosen from heterocyclic groups such as in particular thienyl and pyridyl, phenyl, —NH-phenyl-NH—, —NH-phenyl-CH2-NH—, —NH—CH2-phenyl-CH2-NH— and pyrimidine radicals as defined above.

Among the compounds of formula (I) above, there may be particularly mentioned the compounds characterized in that Ar₁ and Ar₂ represent:
- a quinoline unit optionally substituted with at least
  - a group N(Ra)(Rb) in which Ra and Rb, which are identical or different, represent hydrogen or a C1–C4 alkyl radical or
  - a short-chain alkyl or alkoxy group containing 1 to 4 carbon atoms or
- a quinoline possessing a nitrogen atom in quaternary form or
- a pyridine.

Among the compounds of formula (I) above, there may be mentioned more particularly the compounds characterized in that Ar₁ and Ar₂ represent a group chosen from the following groups: 4-amino- or 4-methylamino-, 4-dimethylamino- or 4-alkoxy-quinolyl or -quinolinium in which the quinolinium nucleus is optionally substituted with a methyl group.

Among the compounds of formula (I) above, there may also be mentioned the compounds characterized in that A is optionally substituted with one or more radicals chosen from halogen atoms and thioalkyl, amino, alkylamino or dialkylamino radicals, radicals in which the alkyl groups possess 1 to 4 carbon atoms and most particularly the compounds characterized in that A is optionally substituted with a methylthio group and optionally with a halogen atom.

The present invention relates in particular to the compounds of formula (IA) as defined above in which: n, m, p and q, which are identical or different, represent the integer 0 or 1

A represents:
- a thienyl or pyridyl radical,
- a phenyl, —NH-phenyl-NH—, —NH-phenyl-CH2-NH—, —NH—CH2-phenyl-CH2-NH—, —CH2-phenyl-CH2— or —CH═CH— radical, or
- a pyrimidyl radical optionally substituted with one or more radicals chosen from halogen atoms and alkylthio radicals having 1 to 4 carbon atoms, R₃ and R'₃, which are identical or different, represent independently of each other hydrogen or a C1–C4 alkyl group Ar₁ and Ar₂, which are identical or different, represent when Ar₁ and Ar₂ are identical:
- a quinoline unit optionally substituted with at least
  - a group N(Ra)(Rb) in which Ra and Rb, which are identical or different, represent hydrogen or a C1–C4 alkyl radical or
  - a short-chain alkyl or alkoxy group containing 1 to 4 carbon atoms or
- a quinoline possessing a nitrogen atom in quaternary form or when Ar₁ and Ar₂ are different
- Ar₁ and Ar₂ both represent one of the possibilities mentioned above for Ar₁ and Ar₂ or
- Ar₁ represents one of the above possibilities and Ar₂ represents
  - a pyridyl nucleus
  - a mono- or bi- or tricyclic aromatic or non-aromatic heterocyclic nucleus containing 0 to 2 heteroatoms per ring provided that at least one heteroatom is present in at least one ring optionally substituted with one or more C1–C4 alkyl groups or with C1–C4 alkylene or C2–C4 alkenylene groups, or one of its salts.

The present invention relates in particular to the compounds of formula (IA) as defined above in which:

n and m, which are identical or different, represent the integer 0 or 1, and p and q represent the integer 1

A represents:
- a thienyl or pyridyl radical,
- a phenyl, —NH-phenyl-NH—, —NH-phenyl-CH2-NH— or —NH—CH2-phenyl-CH2-NH—, radical, or
- a pyrimidyl radical optionally substituted with one or more radicals chosen from halogen atoms and alkylthio radicals having 1 to 4 carbon atoms, R₃ and R'₃, which are identical or different, represent independently of each other hydrogen or a C1–C4 alkyl group Ar₁ and Ar₂, which are identical or different, represent
1. when Ar₁ and Ar₂ are identical:
   - a quinoline unit optionally substituted with at least
     - a group N(Ra)(Rb) in which Ra and Rb, which are identical or different, represent hydrogen or a C1–C4 alkyl radical or
     - a short-chain alkyl or alkoxy group containing 1 to 4 carbon atoms or
   - a quinoline possessing a nitrogen atom in quaternary form or
2. when Ar₁ and Ar₂ are different
   - Ar₁ and Ar₂ both represent one of the possibilities mentioned above for Ar₁ and Ar₂ or Ar₁ represents one of the above possibilities and Ar₂ represents
- a pyridyl nucleus
- a mono- or bi- or tricyclic aromatic or non-aromatic heterocyclic nucleus containing 0 to 2 heteroatoms per ring provided that at least one heteroatom is present in at least one ring optionally substituted with one or more C1–C4 alkyl groups or with C1–C4 alkylene or C2–C4 alkenylene groups, or one of its salts.

The present invention thus relates particularly to the compounds defined above, characterized in that Ar₁ and Ar₂, which are identical or different, represent a group chosen from the 4-amino- or 4-methylamino- or 4-dimethylamino-, or 4-alkoxy-quinolyl or -quinolinium groups in which the quinolinium nucleus is optionally substituted with one or two methyl groups.

Among the compounds of formula (I) of the present invention, there may be mentioned the compounds characterized in that R₃ and R₃' represent hydrogen.

Among the compounds of formula (I) of the present invention, there may be mentioned the compounds characterized in that:

1 Ar₁ represents:
   a quinoline unit substituted with at least
      one group N(Ra)(Rb) in which Ra and Rb, which are identical or different, represent hydrogen or a C1–C4 alkyl radical or
      an short-chain alkyl or alkoxy group containing 1 to 4 carbon atoms or
   a quinoline possessing a nitrogen atom in quaternary form or 2 Ar₂ represents
   a nucleus as defined above but different or
   a pyridyl nucleus
   a quinoline, benzimidazole, indole, benzothiophene, benzofuran, benzothiazole, benzoxazole, carbazole, quinazoline, quinoxaline, piperidyl, piperazinyl, morpholino, azepine and diaza-azepine nucleus, which are optionally substituted by one or more C1–C4 alkyl groups or with C1–C4 alkylene or C2–C4 alkenylene groups or one of its salts.

The following compounds may be mentioned as representative compounds of formula (I):
bis[(4-methoxy-2-methylquinolin-6-yl)-amido]-2,5-thiophenedicarboxylic acid
bis[(4-dimethylamino-2-methylquinolin-6-yl)-amido]-2,5-thiophenedicarboxylic acid
bis[(4-amino-2-methylquinolin-6-yl)-amido]-2,5-thiophenedicarboxylic acid
N,N'-bis(4-amino-2-methylquinolin-6-yl)isophthalamide
N,N'-bis(4-dimethylamino-2-methylquinolin-6-yl)terephthalamide
1-(4-methoxy-2-methylquinolin-6-yl)-3-{3-[3-(4-methoxy-2-methylquinolin-6-yl)ureido]phenyl}urea
1-(4-dimethylamino-2-methylquinolin-6-yl)-3-{4-[3-(4-dimethylamino-2-methylquinolin-6-yl)ureido]phenyl}urea
N,N'-bis(4-amino-2-methyl-6-quinolyl)-2,4-diamino-6-chloro-5-methyl-sulfanylpyrimidine
bis[(4-amino-2-methylquinolin-6-yl)-amido]-2,5-pyridinedicarboxylic acid hydrochloride
bis[(4-amino-2-methylquinolin-6-yl)-amido]-2,5-pyridinedicarboxylic acid
N,N'-bis(4-dimethylamino-2-methylquinolin-6-yl)-but-2-enediamide
bis[(4-dimethylamino-2-methylquinolin-6-yl)-amido]-2,5-pyridinedicarboxylic acid
bis[(4-dimethylamino-2-methylquinolin-6-yl)-amido]-2,4-pyridinedicarboxylic acid
N,N'-bis(4-dimethylamino-2-methylquinolin-6-yl)-1,4-phenylenediacetamide,
bis[(4-amino-2-methylquinolin-6-yl)-amido]-2,6-pyridinedicarboxylic acid hydrochloride
bis[(4-amino-2-methylquinolin-6-yl)amido]-2,6-pyridine dicarboxylic acid
bis[(4-dimethylamino-2-methylquinolin-6-yl)amido]-2,6-pyridinedicarboxylic acid hydrochloride
bis[(4-dimethylamino-2-methylquinolin-6-yl)-amido]-2,6-pyridinedicarboxylic acid or the salts or other salts of these compounds.

The following compounds may be mentioned more particularly as representative compounds of formula (I):
bis[(4-dimethylamino-2-methylquinolin-6-yl)-amido]-2,5-thiophenedicarboxylic acid
N,N'-bis-(4-amino-2-methylquinolin-6-yl)isophthalamide
1-(4-dimethylamino-2-methylquinolin-6-yl)-3-{4-[3-(4-dimethylamino-2-methylquinolin-6-yl)ureido]phenyl}urea
N,N'-bis(4-amino-2-methyl-6-quinolyl)-2,4-diamino-6-chloro-5-methylsulfanylpyrimidine
bis[(4-amino-2-methylquinolin-6-yl)-amido]-2,5-pyridinedicarboxylic acid hydrochloride
bis[(4-amino-2-methylquinolin-6-yl)-amido]-2,5-pyridinedicarboxylic acid
bis-[(4-dimethylamino-2-methylquinolin-6-yl)-amido]-2,5-pyridinedicarboxylic acid
bis[(4-dimethylamino-2-methylquinolin-6-yl)amido]-2,4-pyridinedicarboxylic acid, or the salts or other salts of these compounds.

Among the products of formula (I) of the present invention, there may be mentioned most particularly the compounds defined by the following formula:

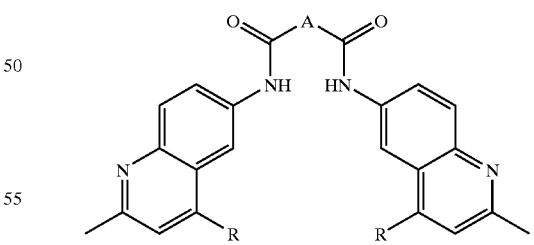

in which R represents a methoxy, amino or dimethylamino group and A represents an aromatic system.

Another subject of the present invention relates to the use of the compounds of formula (I) as pharmaceutical product for human use.

The products of formula (IA) as defined above may be prepared as indicated below for the products of formula (I).

The methods of preparing the compounds of formula (I)

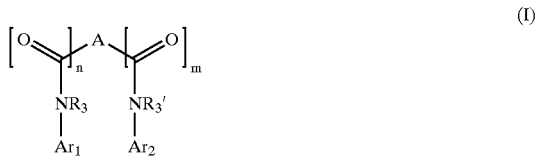

are described below.

The compounds of general formula (I) may be obtained in particular by condensation of diacids and of quinaldines using method A or B which are described below and which are illustrated in the preparation of the examples of the present application below. These methods are not limiting and other methods of activating mono- or diacids in order to form the corresponding amide derivatives may also be used. Reference may thereby be made to 'Comprehensive Organic Transformation' by Richard C. Larock.

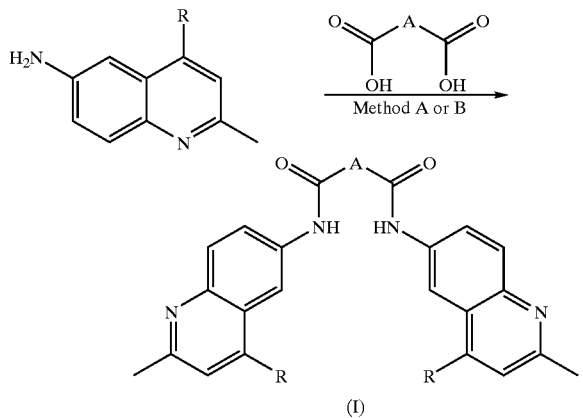

The quinaldines may be prepared in particular as indicated in the following references:

J. Chem. Soc., 1953, 50 such as for example for the preparation of 1-methyl-4,6-diaminoquinaldinium chloride hydrochloride, J. Amer. Chem. Soc., 1948, 70, 4065 such as for example for the preparation of 6-acetamido-4-methoxyquinaldine.

General Method A

According to first method, the products of general formula (I) may be prepared after activation of the diacid with bromotripyrrolidinophosphonium hexafluorophosphate based on the conditions described in *Bioorg. Med. Chem. Lett.* 7(1997) 1903–1908.

General Method B

According to second method, the products of general formula (I) may also be prepared using 4-(4,6-dimethoxy-1,3,5-triazine-2-yl)-4-methylmorpholinium chloride as coupling agent by repeating the conditions described in *Tetrahedron* 2001, 57, 1551–1558.

The 4-(4,6-dimethoxy-1,3,5-triazine-2-yl)-4-methylmorpholinium chloride was prepared by repeating the conditions described in *Tetrahedron* 1999, 55, 13159–13170.

General Method C

Another general route of synthesis of the products described in the descriptions which follow consists in reacting, according to an aromatic nucleophilic substitution, an amine-containing compound (II) with a derivative (III):

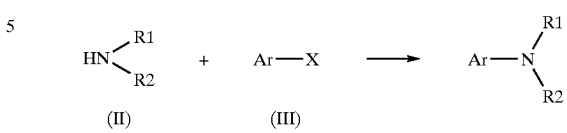

The group Ar is a substituted or unsubstituted aromatic or heteroaromatic derivative.

The substituent X may be a halogen atom or an activated group such as a triflate group ($-OSO_2CF_3$).

The substituents R1 and R2 optionally represent at least the substituents "nitrogen-containing aromatic ring and $R_3$" or "aromatic or non-aromatic ring and $R'_3$".

This reaction may be carried out with or without a catalyst (Pd or Cu for example), with or without an organic or inorganic base.

The amine-containing compound (I) may be optionally activated by converting it to an amide.

It is understood that the compounds of general formula (I) may be obtained in the form of libraries, by applying the methods A, B or C described above in parallel and/or combinatorial chemistry in liquid phase or in solid phase, it being understood that when the work is carried out in solid phase, any one of the reagents is attached beforehand onto a solid support, chosen according to the chemical reaction involved, and that said chemical reaction is followed by an operation of cleaving the product of the reaction from the solid support.

The present invention also relates to therapeutic compositions containing a compound according to the invention, in combination with a pharmaceutically acceptable carrier according to the mode of administration chosen. The pharmaceutical composition may be provided in solid, liquid or liposome form.

Among the solid compositions, there may be mentioned powders, gelatin capsules, and tablets. Among the oral forms, it is also possible to include the solid forms which are protected from the acidic medium of the stomach. The carriers used for the solid forms consist in particular of inorganic carriers such as phosphates, carbonates or organic carriers such as lactose, celluloses, starch or polymers. The liquid forms consist of solutions, suspensions or dispersions. They contain, as dispersive carrier, either water or an organic solvent (ethanol, NMP and the like) or mixtures of surfactants and solvents or of complexing agents and solvents.

The administered dose of the compounds of the invention will be adjusted by the practitioner according to the route of administration to the patient and the condition of the latter.

The compounds of the present invention may be administered alone or mixed with other anticancer agents. Among the possible combinations, there may be mentioned
  alkylating agents and in particular cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine
  platinum derivatives such as in particular cisplatin, carboplatin or oxaliplatin
  antibiotic agents such as in particular bleomycin, mitomycin, dactinomycin,
  antimicrotubule agents such as in particular vinblastine, vincristine, vindesine, vinorelbine, taxoids (paclitaxel and docetaxel)

anthracyclines such as in particular doxorubicin, daunorubicin, idarubicin, epirubicin, mitoxantrone, losoxantrone group I and II topoisomerases such as etoposide, teniposide, amsacrine, irinotecan, topotecan and tomudex, fluoropyrimidines such as 5-fluorouracil, UFT, floxuridine, cytidine analogues such as 5-azacytidine, cytarabine, gemcitabine, 6-mercaptomurine, 6-thioguanine adenosine analogues such as pentostatin, cytarabine or fludarabine phosphate methotrexate and folinic acid enzymes and various compounds such as L-asparaginase, hydroxyurea, trans-retinoic acid, suramine, dexrazoxane, amifostine, herceptin as well as oestrogenic and androgenic hormones antivascular agents such as the derivatives of combretastatin or of coichicine and their prodrug.

It is also possible to combine a radiation treatment with the compounds of the present invention. These treatments may be administered simultaneously, separately or sequentially. The treatment will be adapted to the patient to be treated by the practitioner.

The G-quadruplex stabilizing activity may be determined by a method using the formation of a complex with fluorescein of which the experimental protocol is described below.

Oligonucleotides

All the oligonucleotides, modified or otherwise, were synthesized by Eurogentec S A, Seraing, Belgium. The oligonucleotide FAM+DABCYL carries the catalogue reference OL-0371-0802. It has the sequence: GGGTTAGGGTTAGGGTTAGGG corresponding to 3.5 repeats of the human telomeric unit (strand rich in G). The fluorescein is attached to the 5' end, the DABCYL to the 3' end, by the chemical arms described by Eurogentec. The concentration of the samples is checked by spectrophotometry, recording the absorbance spectrum between 220 and 700 nm and using the molar extinction coefficient provided by the supplier.

Buffers

All the experiments were carried out in a 10 mM sodium cacodylate buffer pH 7.6 containing 0.1 M lithium chloride (or sodium chloride). The absence of fluorescent contamination in the buffer was checked beforehand. The fluorescent oligonucleotide is added at the final concentration of 0.2 $\mu$M.

Study of Fluorescence

All the measurements of fluorescence were carried out on a Spex Fluorolog DM1B apparatus, using an excitation line width of 1.8 nm and an emission line width of 4.5 nm. The samples are placed in a microquartz cuvette of 0.2×1 cm. The temperature of the sample is controlled by an external water bath. The oligonucleotide alone was analyzed at 20, 30, 40, 50, 60, 70 and 80° C. The emission spectra are recorded using an excitation wavelength of 470 nm. The excitation spectra are recorded using either 515 nm or 588 nm as emission wavelength. The spectra are corrected for the response of the instrument by reference curves. A high extinction (80–90%) of the fluorescence of fluorescein at room temperature is observed, in agreement with an intramolecular folding of the oligonucleotide at 20° C. in the form of a G-quadruplex, which induces juxtaposition of its 5' and 3' ends which are respectively linked to fluorescein and to DABCYL. This juxtaposition causes an already-described phenomenon of extinction of fluorescence which is used for "Molecular Beacons".

Fluorescence Tm:

An oligonucleotide stock solution at the strand concentration of 0.2 $\mu$M in 0.1 M LiCl, 10 mM cacodylate buffer, pH 7.6, is prepared beforehand, heated briefly at 90° C. and slowly cooled to 20° C., and then distributed in aliquots of 600 $\mu$l in the fluorescence cuvettes. 3 $\mu$l of water (for the control) or 3 $\mu$l of test product (stock at 200 $\mu$M, final concentration 1 $\mu$M) are then added and mixed. The samples are then allowed to incubate for at least 1 hour at 20° C. before each measurement. The use of longer incubation times (up to 24 hours) has no influence on the result obtained.

Each experiment allows the measurement of only one sample. The latter is first incubated at an initial temperature of 20° C., heated to 80° C. over 38 minutes, left for 5 minutes at 80° C. and then cooled to 20° C. over 62 minutes. During this time, the fluorescence is measured simultaneously at two emission wavelengths (515 nm and 588 nm) using 470 nm as excitation wavelength. A measurement is carried out every 30 seconds. The temperature of the water bath is recorded in parallel, and the fluorescence profile as a function of the temperature is reconstituted from these values. The fluorescence profiles are then normalized between 20° C. and 80° C., and the temperature for which the intensity of emission at 515 nm is the mean of those at high and low temperature is called Tm. Under these conditions, the Tm of the reference sample without addition of product is 44° C. in a lithium chloride buffer. This temperature is increased to more than 55° C. in a sodium chloride buffer. The addition of a G-quadruplex stabilizing compound induces an increase in the Tm. This increase is judged to be significant if it is greater than 3°.

The antitelomerase biological activity is determined by the following experimental protocol:

Preparation of the Extract Enriched in Human Telomerase Activity

The leukemia line HL60 is obtained from ATCC (American Type Culture Collection, Rockville USA). The cells are cultured in suspension in RPMI 1640 medium containing L-Glutamine at 2 mM, Penicillin 200 U/ml, streptomycin 200 $\mu$g/ml, gentamycin 50 $\mu$g/ml and supplemented with 10% heat-inactivated foetal calf serum.

An aliquot of $10^5$ cells is centrifuged at 300×G and the supernatant discarded. The cell pellet is resuspended by several successive pipettings in 200 $\mu$l of lysis buffer containing 0.5% CHAPS, 10 mM Tris-HCl pH 7.5, 1 mM MgCl$_2$, 1 mM EGTA, 5 mM $\beta$-mercaptoethanol, 0.1 mM PMSF and 10% glycerol and is stored in ice for 30 minutes. The lysate is centrifuged at 160,000×G for 20 minutes at 4° C. and 160 $\mu$l of supernatant is recovered. The proteins in the extract are assayed by the Bradford method. The extract is stored at −80° C.

Assay of the Telomerase Activity

The inhibition of the telomerase activity is determined by a protocol for extension of the oligonucleotide TS ($^{5'}$AATCGTTCGAGCAGAGTT$^{3'}$), in the presence of a cellular extract enriched in telomerase activity and compounds which are added at various concentrations (10, 1, 0.1 and 0.01 $\mu$g/ml). The extension reaction is followed by a PCR amplification of the extension products with the aid of the oligonucleotides TS and CXext ($^{5'}$GTGCCCTTACCCTTACCCTTACCCTAA$^{3'}$).

The reaction medium is prepared based on the following composition:

| | |
|---|---|
| Tris HCl pH 8.3 | 20 mM |
| MgCl2 | 1.5 mM |
| Tween 20 | 0.005% (W/V) |
| EGTA | 1 mM |
| dATP | 50 μM |
| dGTP | 50 μM |
| dCTP | 50 μM |
| dTTP | 50 μM |
| Oligonucleotide TS | 2 μg/ml |
| Oligonucleotide CXext | 2 μg/ml |
| Bovine serum albumin | 0.1 mg/ml |
| Taq DNA polymerase | 1 U/ml |
| alpha 32P dCTP (3000 Ci/mmol) | 0.5 μl |
| Telomerase extract | 200 ng in a volume of 10 μl |
| Test product or solvent | in a volume of 5 μl |
| Double distilled water QS | 50 μl |

The oligonucleotides are obtained from Eurogentec (Belgium) and are stored at −20° C. at a stock concentration of 1 mg/ml in distilled water.

The reaction samples are assembled in 0.2 ml PCR tubes and one drop of paraffin oil is deposited on each of the reactions of the experiment before closing the tubes.

The reaction samples are then incubated in a Cetus 4800-type PCR apparatus under the following temperature conditions:

15 minutes at 30° C.,
1 minute at 90° C.,
followed by 30 cycles of,
30 seconds at 94° C.,
30 seconds at 50° C.,
and 1 minute 30 seconds at 72° C.,
followed by a final cycle of 2 minutes at 72° C.

For each of the samples, an aliquot of 10 μl is pipetted under the oil layer and mixed with 5 μl of a loading buffer containing:

| TBE | 3X |
|---|---|
| glycerol | 32% (W/V) |
| Bromophenol blue | 0.03% |
| Xylene cyanol | 0.03% |

The samples are then analyzed by electrophoresis on 12% acrylamide gel in a 1×TBE buffer for 1 hour at a voltage of 200 volts, with the aid of a Novex electrophoresis system.

The acrylamide gels are then dried on a sheet of whatmann 3MM paper at 80° C. for 1 hour.

The analysis and the quantification of the reaction products are carried out with the aid of an Instant Imager apparatus (Pacard).

For each compound concentration tested, the results are expressed as percentage inhibition of the reaction and calculated from the untreated enzymatic control and from the enzyme-free sample (blank) according to the following formula:

(Compound Value−blank value/enzymatic control value−blank value)×100.

The concentration of compound inducing a 50% inhibition of the telomerase reaction (IC50) is determined with the aid of a semilogarithmic graphical representation of the inhibition values obtained as a function of each of the compound concentrations tested.

A compound is considered to be active as an antitelomerase agent when the quantity inhibiting 50% of the telomerase reaction is in particular less than 5 μM.

The cytotoxic Biological Activity on Human Tumor Lines is Determined According to the Following Experimental Protocol:

The human cell lines KB and A549 are obtained from ATCC (American Type Culture Collection, Rockville USA). The A549 cells are cultured in a layer in a culture flask in RPMI 1640 medium containing L-Glutamine at 2 mM, Penicillin 200 U/ml, streptomycin 200 μg/ml and supplemented with 10% heat-inactivated foetal calf serum. The KB cells are cultured in a layer in a culture flask in Dulbelco's medium containing L-Glutamine at 2 mM, Penicillin 200 U/ml, streptomycin 200 μg/ml and supplemented with 10% heat-inactivated foetal calf serum.

The cells at the exponential growth phase are trypsinized, washed in 1×PBS and are inoculated in 96-well microplates (Costar) in an amount of 4×10$^4$ cells/ml for A549 and of 1.5×10$^4$ cells/ml (0.2 ml/well) and then incubated for 96 hours in the presence of variable concentrations of product to be studied (10, 1, 0.1 and 0.01 μg/ml, each point in quadruplicate). 16 hours before the end of the incubation, 0.02% final of neutral red is added to each well. At the end of the incubation, the cells are washed with 1×PBS and lysed with 1% sodium lauryl sulfate. The cellular incorporation of the dye, which reflects cellular growth, is evaluated by spectrophotometry at a wavelength of 540 nm for each sample with the aid of a Dynatech MR5000 reading apparatus.

For each compound concentration tested, the results are expressed as percentage inhibition of cellular growth and calculated from the untreated control and the culture medium free of cells (blank) according to the following formula:

(Compound Value−blank value/cell control value−blank value)×100.

The concentration of compound inducing a 50% inhibition of growth (IC50) is determined with the aid of a semilogarithmic graphical representation of the inhibition values obtained as a function of each of the compound concentrations tested.

A compound is considered to be active as cytotoxic agent if the concentration inhibiting the growth of the tumor cells tested by 50% is in particular less than 10 μM.

The following nonlimiting examples are given to illustrate the invention.

EXAMPLE 1

Preparation of bis[(4-methoxy-2-methylquinolin-6-yl)amido]-2,5-thiophenedicarboxylic acid

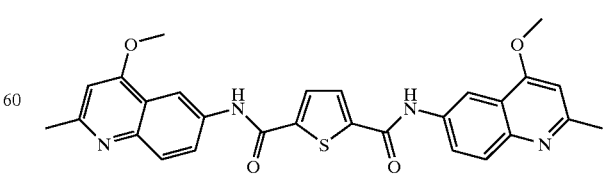

Bromotripyrrolidinophosphonium hexafluorophosphate (338 mg, 0.72 mmol) and 0.304 mL (1.7 mmol) of N,N-diisopropylethylamine are successively added to a solution of 50 mg (0.29 mmol) of 2,5-thiophenedicarboxylic acid in 1.5 mL of dimethylformamide, under an inert argon atmosphere, at a temperature in the region of 20° C. The solution obtained is stirred at a temperature in the region of 20° C. for about 15 minutes. 164 mg (0.87 mmol) of 4-methoxy-6-aminoquinaldine are added, the stirring is maintained at a temperature in the region of 20° C. for about 12 hours. The reaction mixture is concentrated to dryness under reduced pressure (2.7 kPa) at a temperature in the region of 40° C. The residue obtained is taken up in the hot state in 8 mL of acetonitrile. The medium is allowed to cool, filtered on sintered glass and the solid obtained is washed with 3 mL of diisopropyl ether; 150 mg of a brown solid are obtained. A portion of this solid (50 mg) is taken up in 2 mL of a ternary mixture (chloroform/methanol/aqueous solution of ammonia at 20%) (12/6/1 by volume). The insoluble matter is filtered on sintered glass. 15 mg of bis[(4-methoxy-2-methylquinolin-6-yl)-amido]-2,5-thiophenedicarboxylic acid are thus obtained in the form of a beige solid whose characteristics are the following:

$^1$H NMR spectrum (300 MHz, $(CD_3)_2SO$ d6, δ in ppm): 2.63 (s: 6H); 4.08 (s: 6H); 6.96 (s: 2H); 7.88 (d, J=9 Hz: 2H); 8.06 (dd, J=9 and 2 Hz: 2H); 8.16 (s: 2H); 8.62 (d, J=2 Hz: 2H) 10.69 (unresolved complex: 2H).

EXAMPLE 2

Preparation of bis[(4-dimethylamino-2-methylquinolin-6-yl)amido]-2,5-thiophenedicarboxylic acid

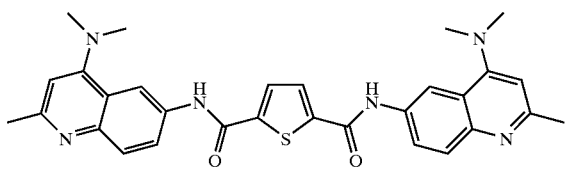

Bromotripyrrolidinophosphonium hexafluorophosphate (271 mg, 0.58 mmol) and 0.304 mL (1.7 mmol) of N,N-diisopropylethylamine are successively added to a solution of 50 mg (0.29 mmol) of 2,5-thiophenedicarboxylic acid in 1.5 mL of dimethylformamide, under an inert argon atmosphere, at a temperature in the region of 20° C. The solution obtained is stirred at a temperature in the region of 20° C. for about 15 minutes. 116 mg (0.58 mmol) of 4-dimethylamino-6-aminoquinaldine are added, and the stirring is maintained at a temperature in the region of 20° C. for about 12 hours. The reaction mixture is filtered on sintered glass, the solid obtained is successively washed with acetonitrile (2 mL) and then with diisopropyl ether (2 mL), 40 mg of bis[(4-dimethylamino-2-methylquinolin-6-yl)-amido]-2,5-thiophenedicarboxylic acid are thus obtained in the form of a yellow solid whose characteristics are the following:

$^1$H NMR spectrum (300 MHz, $(CD_3)_2SO$ d6, δ in ppm): 2.62 (s: 6H); 3.21 (unresolved complex: 12H); 6.87 (s: 2H); 7.89 (d, J=9 Hz: 2H); 8.06 (broad d, J=9 Hz: 2H); 8.20 (s: 2H); 8.77 (broad s: 2H); 10.82 (unresolved complex: 2H).

EXAMPLE 3

Preparation of bis[(4-amino-2-methylquinolin-6-yl)amido]-2,5-thiophenedicarboxylic acid

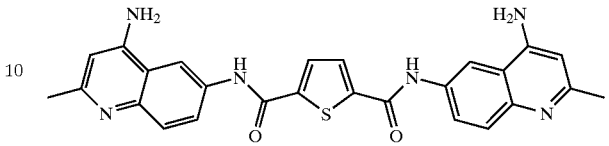

Bromotripyrrolidinophosphonium hexafluorophosphate (270 mg, 0.58 mmol) and 0.304 mL (1.7 mmol) of N,N-diisopropylethylamine are successively added to a solution of 50 mg (0.29 mmol) of 2,5-thiophenedicarboxylic acid in 1.5 mL of dimethylformamide, under an inert argon atmosphere, at a temperature in the region of 20° C. The solution obtained is stirred at a temperature in the region of 20° C. for about 15 minutes. 100 mg (0.58 mmol) of 2-methylquinoline-4,6-diamine are added, and the stirring is maintained at a temperature in the region of 20° C. for about 12 hours. The reaction medium is precipitated with acetonitrile (1 mL), the insoluble matter is filtered on sintered glass and then washed with diisopropyl ether (1 mL). 96 mg of solid are obtained. A portion of the solid (26 mg) is taken up in ethanol (1 mL). The insoluble matter is filtered on sintered glass. 16 mg of bis[(4-amino-2-methylquinolin-6-yl)amido]-2,5-thiophenedicarboxylic acid are thus obtained in the form of a beige solid whose characteristics are the following:

$^1$H NMR spectrum (300 MHz, $(CD_3)_2SO$ d6, δ in ppm): 2.55 (s: 6H); 6.57 (s: 2H); 7.82 (d, J=9 Hz: 2H); 8.02 (broad d, J=9 Hz: 2H); 8.24 (s: 2H); 8.70 (broad s: 2H); 10.93 (unresolved complex: 2H).

EXAMPLE 4

Preparation of bis[(4-amino-2-methylquinolin-6-yl)amido]-3,5-pyridinedicarboxylic acid

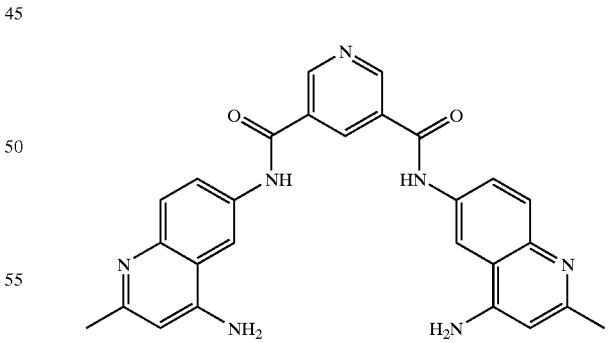

Bromotripyrrolidinophosphonium hexafluorophosphate (270 mg, 0.58 mmol) and 0.304 mL (1.7 mmol) of N,N-diisopropylethylamine are successively added to a solution of 48 mg (0.29 mmol) of 3,5-pyridinedicarboxylic acid in 1.5 mL of dimethylformamide, under an inert argon atmosphere, at a temperature in the region of 20° C. The solution obtained is stirred at a temperature in the region of 20° C. for about 10 minutes. 100 mg (0.58 mmol) of 2-methylquinoline-4,6-diamine are added, and the stirring is maintained at a temperature in the region of 20° C. for about 12 hours. The reaction mixture is filtered on sintered glass, the solid obtained is successively washed with acetonitrile (3 mL) and then with diisopropyl ether (3 mL), 55 mg of a solid are thus obtained which are taken up in 2 mL of a ternary mixture (chloroform/methanol/aqueous solution of ammonia at 20%) (12/6/1 by volume). The insoluble matter is filtered on sintered glass. 47 mg of bis[(4-amino-2-methylquinolin-6-yl)amido]-3,5-pyridinedicarboxylic acid are thus obtained in the form of a beige powder whose characteristics are the following:

$^1$H NMR spectrum (400 MHz, $(CD_3)_2SO$ d6, at a temperature of 373K, δ in ppm): 2.55 (s: 6H); 6.61 (s: 2H); 7.09 (unresolved complex: 2H); 7.82 (broad d, J=8.5 Hz: 2H); 8.01 (broad d, J=8.5 Hz: 2H); 8.55 (broad s: 2H); 9.00 (unresolved complex: 1H); 9.36 (broad s: 2H); 10.65 (unresolved complex: 1H).

EXAMPLE 5

Preparation of N,N'-bis(4-dimethylamino-2-methylquinolin-6-yl)-isophthalamide

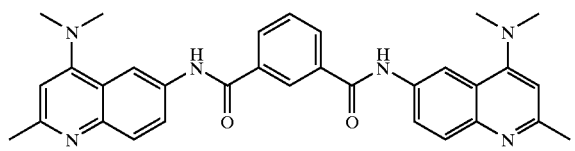

Bromotripyrrolidinophosphonium hexafluorophosphate (337 mg, 0.72 mmol) and 0.379 mL (2.17 mmol) of N,N-diisopropylethylamine are successively added to a solution of 60 mg (0.36 mmol) of isophthalic acid in 2 mL of dimethylformamide, under an inert argon atmosphere, at a temperature in the region of 20° C. The solution obtained is stirred at a temperature in the region of 20° C. for about 10 minutes. 145 mg (0.72 mmol) of 4-dimethylamino-6-aminoquinaldine are added, and the stirring is maintained at a temperature in the region of 20° C. for about 12 hours. The reaction mixture is concentrated to dryness under reduced pressure (2.7 kPa) at a temperature in the region of 40° C. The residue obtained is taken up in methanol and then deposited on a BOND-ELUT VARIAN cartridge with the reference 1225-6027 containing 5 g of SCX phase conditioned in methanol. The cartridge is washed with methanol and then eluted with 2M ammoniacal methanol. The ammoniacal fractions are concentrated to dryness under reduced pressure (2.7 kPa) at a temperature in the region of 40° C. 49 mg of N,N'-bis(4-dimethylamino-2-methylquinolin-6-yl)isophthalamide are thus obtained in the form of a cream-colored solid whose characteristics are the following:

$^1$H NMR spectrum (300 MHz, $(CD_3)_2SO$ d6, δ in ppm): 2.62 (s: 6H); 3.24 (unresolved complex: 12H); 6.86 (s: 2H); 7.78 (t, J=8 Hz: 1H); 7.88 (d, J=9 Hz: 2H); 8.17 (very broad d, J=8 Hz: 2H); 8.25 (dd, J=9 and 1.5 Hz: 2H); 8.70 (broad s: 1H); 8.83 (broad s: 2H); 10.87 (broad s: 2H).

EXAMPLE 6

Preparation of N,N'-bis(4-amino-2-methylquinolin-6-yl)-isophthalamide

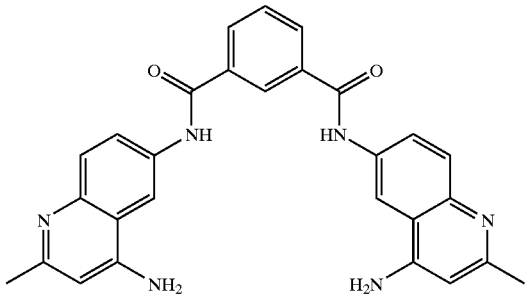

Bromotripyrrolidinophosphonium hexafluorophosphate (561 mg, 1.2 mmol) and 0.630 mL (3.6 mmol) of N,N-diisopropylethylamine are successively added to a solution of 100 mg (0.60 mmol) of isophthalic acid in 3 mL of dimethylformamide, under an inert argon atmosphere, at a temperature in the region of 20° C. The solution obtained is stirred at a temperature in the region of 20° C. for about 10 minutes. 208 mg (1.2 mmol) of 4,6-diamino-2-methylquinoline are added, and the stirring is maintained at a temperature in the region of 20° C. for about 12 hours. The reaction mixture is concentrated to dryness under reduced pressure (2.7 kPa) at a temperature in the region of 40° C. The residue obtained is taken up in 5 mL of acetonitrile, filtered on sintered glass and then washed with 3 mL of diisopropyl ether. The brown powder thus obtained is purified by FLASH chromatography on a BOND-ELUT cartridge (27 mm in diameter) sealed with 20 g of conditioned silica (15–35 μm) and then eluted with a (dichloromethane/2 M ammoniacal methanol) (75-25 by volume) mixture. The fractions containing the desired product are combined and concentrated to dryness under reduced pressure (2.7 kPa) at 40° C. 77 mg of N,N'-bis(4-amino-2-methylquinolin-6-yl) isophthalamide are thus obtained in'the form of a brown powder whose characteristics are the following:

$^1$H NMR spectrum (300 MHz, $(CD_3)_2SO$ d6, δ in ppm): 2.48 (s: 6H); 6.52 (s: 2H); 7.27 (unresolved complex: 4H); 7.76 (d, J=9 Hz: 2H); 7.78 (t, J=7.5 Hz: 1H); 7.92 (dd, J=9 and 2 Hz: 2H); 8.25 (dd, J=7.5 and 1.5 Hz: 2H); 8.56 (broad d, J=2 Hz: 2H); 8.70 (mt: 1H); 10.71 (broad s: 2H)

EXAMPLE 7

Preparation of N,N'-bis(4-dimethylamino-2-methylquinolin-6-yl)-terephthalamide

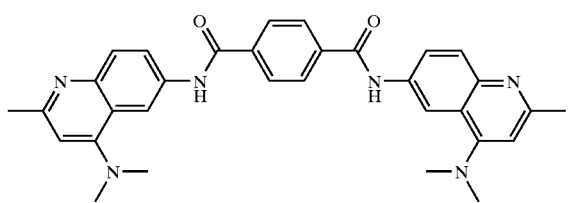

4-(4,6-Dimethoxy-1,3,5-triazine-2-yl)-4-methylmorpholinium chloride (177 mg) is added to a solution of 48 mg (0.29 mmol) of terephthalic acid and 128 mg (0.64 mmol) of 4-dimethylamino-6-aminoquinaldine in 6 mL of dimethylformamide, at a temperature in the region of 20° C. The mixture obtained is stirred at a temperature in the region of 20° C. for about 12 hours. The reaction mixture is successively taken up in 2 mL of acetonitrile and 2 mL of diisopropyl ether, and the precipitate thus obtained is slowly filtered on a 6 mL BOND-ELUT cartridge filled with sintered material. The insoluble matter obtained is washed with diisopropyl ether and then dried under argon. 154 mg of N,N'-bis(4-dimethylamino-2-methylquinolin-6-yl)-terephthalamide are thus obtained in the form of a beige powder of whose characteristics are the following:

$^1$H NMR spectrum (400 MHz, $(CD_3)_2SO$ d6, at a temperature of 373K, δ in ppm): 2.70 (s: 6H); 3.44 (s: 12H); 6.87 (s: 2H); 7.98 (d, J=9 Hz: 2H); 8.23 (s: 4H); 8.27 (dd, J=9 and 1.5 Hz: 2H); 8.94 (broad s: 2H); 10.64 (broad s: 2H).

EXAMPLE 8

Preparation of 1-(4-methoxy-2-methylquinolin-6-yl)-3-{3-[3-(4-methoxy-2-methylquinolin-6-yl)ureido]phenyl}urea

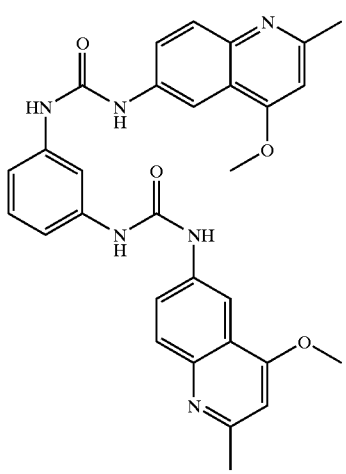

A solution of 50 mg of 1,3-phenylene diisocyanate and 235.1 mg of 6-amino-4-methoxy-2-methylquinoline in 1 mL of dimethylformamide is stirred at a temperature in the region of 20° C. for 3 hours. The reaction mixture is filtered on sintered glass, and the solid residue is rinsed with 1 mL of dimethylformamide. The filtrate thus obtained is diluted with 2 mL of dimethylformamide, and then 333 mg of polystyrene-isocyanate resin (Argonaut, 1.49 mmol/g) and 419 mg of polystyrene-trisamine resin (Argonaut, 3.75 mmol/g) are added. The suspension obtained is stirred at a temperature in the region of 20° C. for 19 hours, filtered on sintered glass, and then the solid residue is washed with 20 mL of a dichloromethane-methanol (90-10 by volume) mixture. The filtrate obtained is concentrated under reduced pressure (2.7 kPa) at a temperature in the region of 50° C. 0.404 g of a violet-brown suspension is thus obtained. 7 mL of dichloromethane, 2 mL of dimethylformamide and 333 mg of polystyrene-isocyanate resin (Argonaut, 1.49 mmol/g) are added to this reaction mixture. The suspension obtained is stirred at a temperature in the region of 60° C. for 19 hours, filtered on sintered glass, and then the solid residue is washed with a dichloromethane-methanol (90-10 by volume) mixture. The filtrate obtained is concentrated under reduced pressure (2.7 kPa) at a temperature in the region of 50° C., taken up in a dichloromethane-methanol mixture, and concentrated under reduced pressure (2.7 kPa) at a temperature in the region of 50° C. 81 mg of a violet powder are thus obtained, which powder is purified by flash chromatography on a silica gel column (Flashpack, 10 g of silica, particle size 0.015–0.035 mm), eluting with a dichloromethane-methanol (90-10 by volume) mixture. The fractions containing the desired product are combined and concentrated to dryness under reduced pressure (2.7 kPa) at a temperature in the region of 50° C. 54 mg of 1-(4-methoxy-2-methylquinolin-6-yl)-3-{3-[3-(4-methoxy-2-methylquinolin-6-yl)ureido]phenyl}urea are obtained in the form of a pinkish-white powder.

$^1$H NMR spectrum (300 MHz, $(CD_3)_2SO$ d6, δ in ppm): 2.63 (s: 6H); 4.08 (s: 6H); 6.96 (s: 2H); 7.88 (d, J=9 Hz: 2H); 8.06 (dd, J=9 and 2 Hz: 2H); 8.16 (s: 2H); 8.62 (d, J=2 Hz: 2H); 10.69 (unresolved complex: 2H).

EXAMPLE 9

Preparation of 1-(4-dimethylamino-2-methylquinolin-6-yl)-3-{4-[3-(4-dimethylamino-2-methylquinolin-6-yl)ureido]phenyl}urea

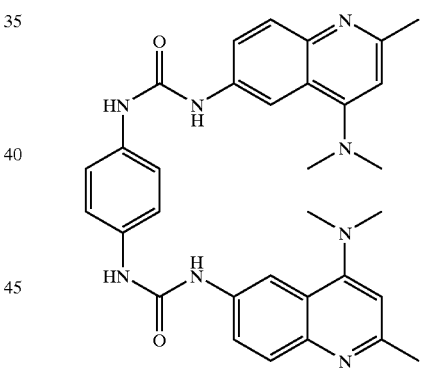

A solution of 25 mg of 1,4-phenylene diisocyanate and 62.8 mg of 6-amino-4-dimethylamino-2-methylquinoline in 1 mL of dimethylformamide is stirred at a temperature in the region of 20° C. for 5 hours. 2 mL of dimethylformamide, 218 mg of polystyrene-isocyanate resin (Argonaut, 1.49 mmol/g) and 42 mg of polystyrene-trisamine resin (Argonaut, 3.75 mmol/g) are then added to the reaction mixture. The suspension obtained is stirred at a temperature in the region of 20° C. for 17 hours, filtered on sintered glass, and then the solid residue is washed with 10 mL of a dichloromethane-methanol (90-10 by volume) mixture. The filtrate obtained is concentrated under air stream at a temperature in the region of 50° C. 42.4 mg of 1-(4-dimethylamino-2-methylquinolin-6-yl)-3-{4-[3-(4-dimethylamino-2-methylquinolin-6-yl)ureido]phenyl}urea are thus obtained in the form of a yellow solid.

¹H NMR spectrum (300 MHz, (CD₃)₂SO d6, δ in ppm):
2.56 (s: 6H); 3.05 (unresolved complex: 12H); 6.79 (s: 2H); 7.42 (d, J=9 Hz: 4H); 7.60 (dd, J=9 and 2 Hz: 2H); 7.77 (d, J=9 Hz: 2H); 8.38 (unresolved complex: 2H); 8.70 (broad s: 2H); 8.99 (unresolved complex: 2H).

EXAMPLE 10

Preparation of 1-(4-dimethylamino-2-methylquinolin-6-yl)-3-{3-[3-(4-dimethylamino-2-methylquinolin-6-yl)ureido]phenyl}urea

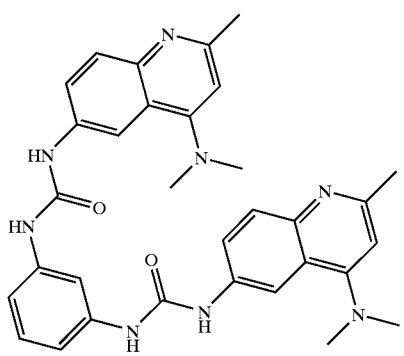

A solution of 25 mg of 1,3-phenylene diisocyanate and 125.8 mg of 6-amino-4-dimethylamino-2-methylquinoline in 2 mL of dimethylformamide is stirred at a temperature in the region of 20° C. for about 5 hours. 2 mL of dimethylformamide, 437 mg of polystyrene-isocyanate resin (Argonaut, 1.49 mmol/g) and 83.2 mg of polystyrene-trisamine resin (Argonaut, 3.75 mmol/g) are then added to the reaction medium. The suspension obtained is stirred at a temperature in the region of 20° C. for about 20 hours, filtered on sintered glass and then the solid residue is washed with 10 mL of a dichloromethane-methanol (90-10 by volume) mixture. The filtrate obtained is concentrated under reduced pressure (2.7 kPa) at a temperature in the region of 50° C., and the residue obtained is successively co-evaporated under the same conditions as above with toluene, water, dichloromethane and methanol. 113 mg of a yellow solid are thus obtained. This solid is taken up in 2 mL of dimethyl sulfoxide, filtered on sintered glass, and filtered on a Celite cartridge. The insoluble residue is washed with 1 mL of dimethyl sulfoxide and 1 mL of methanol. The filtrate obtained is centrifuged (5 minutes at 3000 revolutions/min), and the supernatant liquid is purified by HPLC in 7 injections (column: C18 Waters, 5 µM; eluent: elution gradient water-acetonitrile-TFA (0.07%) from 95-5 to 5-95 over 25 minutes). The fractions containing the desired product are combined and concentrated to dryness under reduced pressure (2.7 kPa) at a temperature in the region of 50° C. 25.8 mg of 1-(4-dimethylamino-2-methylquinolin-6-yl)-3-{3-[3-(4-dimethylamino-2-methylquinolin-6-yl)ureido]phenyl}urea are obtained in the form of a cream-colored solid.

¹H NMR spectrum (300 MHz, (CD₃)₂SO d6, δ in ppm):
2.65 (s: 6H); 3.41 (s: 12H); 6.88 (s: 2H); from 7.15 to 7.30 (mt: 3H); 7.67 (unresolved complex: 1H); 7.83 (mt: 4H); 8.69 (broad s: 2H); 9.09 (broad s: 2H); 9.35 (unresolved complex: 2H).*

EXAMPLE 11

Preparation of 1-(4-dimethylamino-2-methylquinolin-6-yl)-3-{4-[3-(4-dimethylamino-2-methylquinolin-6-yl)ureido]tolyl}urea

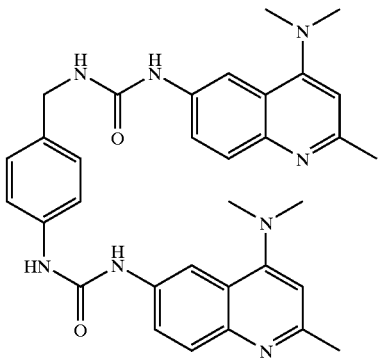

A solution of 0.025 mL of 1,4-tolylene diisocyanate and 70.4 mg of 6-amino-4-dimethylamino-2-methylquinoline in 2 mL of dimethylformamide is stirred at a temperature in the region of 20° C. for about 18 hours. 2 mL of dimethylformamide, 232 mg of polystyrene-isocyanate resin (Argonaut, 1.51 mmol/g) and 47 mg of polystyrene-trisamine resin (Argonaut, 3.75 mmol/g) are then added to the reaction medium. The suspension obtained is stirred at a temperature in the region of 20° C. for about 23 hours, filtered on sintered glass, and then the solid residue is washed with 4 times 2 mL of a dichloromethane-methanol (90-10 by volume) mixture. The filtrate obtained is concentrated under an air stream at a temperature in the region of 40° C., and then reconcentrated under reduced pressure (2.7 kPa) at a temperature in the region of 40° C. 83 mg of 1-(4-dimethylamino-2-methylquinolin-6-yl)-3-{4-[3-(4-dimethylamino-2-methylquinolin-6-yl)ureido]-tolyl}urea are thus obtained in the form of a brown sticky solid.

¹H NMR spectrum (300 MHz, (CD₃)₂SO d6, δ in ppm):
2.57 (s: 6H); 3.06 (s: 6H); 3.08 (s: 6H); 4.30 (d, J=5.5 Hz: 2H); 6.71 (mt: 1H); 6.77 (s: 1H); 6.79 (s: 1H); 7.28 (d, J=8.5 Hz: 2H); 7.47 (d, J=8.5 Hz: 2H); 7.60 (mt: 2H); 7.74 (d, J=9 Hz: 1H); 7.78 (d, J=9 Hz: 1H); 8.39 (broad s: 2H); 8.87 (broad s: 1H); 8.97 (broad s: 1H); 9.11 (broad s: 1H).

EXAMPLE 12

Preparation of the (4-dimethylamino-2-methylquinolin-6-ylamino)amide of 6-(4-dimethylamino-2-methylquinolin-6-ylamino)-2-methylsulfanylpyrimidine-4-carboxylic acid

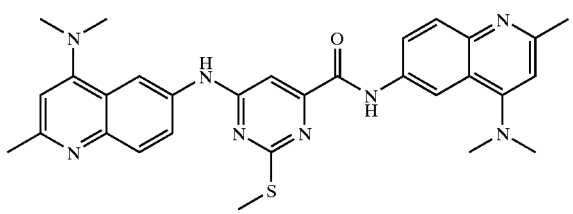

A solution of 54 mg of 6-amino-4-dimethylamino-2-methylquinoline, 50 mg of the (4-dimethylamino-2-methylquinolin-6-ylamino)amide of 6-chloro-2-methylsulfanylpyrimidine-4-carboxylic acid, 32 mg of sodium carbonate in 3 mL of dimethylformamide is heated at a temperature in the region of 80° C. for about 20 hours. After cooling to a temperature in the region of 20° C., 10 mL of water and 10 mL of dichloromethane are added to the reaction medium. After decantation, the organic phase is dried over sodium sulfate, filtered and then concentrated under reduced pressure (2.7 kPa) at a temperature in the region of 40° C. The residue obtained is purified by HPLC (column: C18 Waters, 5 μM, 50×19 mm; eluent: elution gradient water-acetonitrile-TFA (0.07%) from 95-5 to 5-95 over 30 minutes). The fractions containing the desired product are combined and concentrated to dryness under reduced pressure (2.7 kPa) at a temperature in the region of 40° C. 23 mg of the (4-dimethylamino-2-methylquinolin-6-ylamino)amide of 6-(4-dimethylamino-2-methylquinolin-6-ylamino)-2-methylsulfanylpyrimidine-4-carboxylic acid are obtained.

$^1$H NMR spectrum (300 MHz, $(CD_3)_2SO$ d6, δ in ppm): 2.64 (s: 6H); 2.73 (s: 3H); 3.45 (s: 6H); 3.48 (s: 6H); 6.81 (broad s: 1H); 6.84 (broad s: 1H); 7.28 (s: 1H); 7.89 (broad d, J=8.5 Hz: 2H); 7.98 (broad d, J=8.5 Hz: 1H); 8.22 (dd, J=8.5 and 2 Hz: 1H); 8.90 (broad d, J=2 Hz: 1H) 8.97 (broad s: 1H); 10.60 (broad s: 1H); 10.80 (broad s: 1H); 14.12 (unresolved complex: 1H).

4-Dimethylamino-2-methylquinolin-6-ylamino)amide of 6-chloro-2-methylsulfanylpyrimidine-4-carboxylic acid may be prepared by carrying out the procedure in the following manner:

1.6 mL of triethylamine and 800 mg of 6-amino-4-dimethylamino-2-methylquinoline are successively added to a solution of 400 mg of 6-chloro-2-methylsulfanylpyrimidine-4-carboxylic acid chloride in 20 mL of tetrahydrofuran, at a temperature in the region of 20° C. After stirring for about 20 hours at a temperature in the region of 20° C., the reaction medium is diluted with 20 mL of water and then concentrated under reduced pressure (2.7 kPa) at a temperature in the region of 40° C. The residue obtained is dissolved in 20 mL of dimethyl sulfoxide and purified by HPLC (column: C18 Waters, 5M, 50×19 mm; eluent: elution gradient water-acetonitrile-TFA (0.07%) from 95-5 to 5-95 over 30 minutes). The fractions containing the desired product are combined and concentrated to dryness under reduced pressure (2.7 kPa) at a temperature in the region of 40° C. 520 mg of the (4-dimethylamino-2-methylquinolin-6-ylamino) amide of 6-chloro-2-methylsulfanylpyrimidine-4-carboxylic acid are obtained. 1.1 mL of N,N-dimethylaniline are added, at a temperature in the region of 20° C., to a solution of 2 g of 6-hydroxy-2-methylsulfanylpyrimidine-4-carboxylic acid in 10 mL of phosphoryl chloride. The blue reaction mixture thus obtained is heated at a temperature in the region of 100° C. for about 2.5 hours. The excess phosphoryl chloride is then distilled at atmospheric pressure. The 6-chloro-2-methylsulfanylpyrimidine-4-carboxylic acid chloride thus obtained is used as it is for the next step.

EXAMPLE 13

(4-dimethylamino-2-methylquinolin-6-ylamino) amide of 6-(4-methoxy-2-methylquinolin-6-ylamino)-2-methylsulfanylpyrimidine-4-carboxylic acid

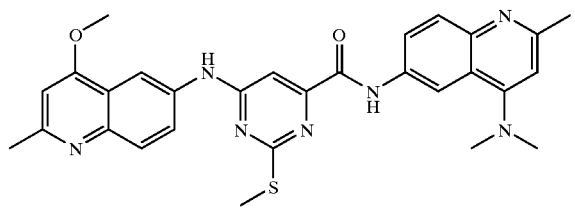

The title compound is prepared by following the procedures of Example 12 and by employing the following materials in amounts as specified:

Starting with 19 mg of 6-amino-4-methoxy-2-methylquinoline, 50 mg of (4-dimethylamino-2-methylquinolin-6-ylamino)amide of 6-chloro-2-methylsulfanylpyrimidine-4-carboxylic acid, 32 mg of sodium carbonate and 3 mL of dimethylformamide, 15 mg of (4-dimethylamino-2-methylquinolin-6-ylamino)amide of 6-(4-methoxy-2-methylquinolin-6-ylamino)-2-methylsulfanylpyrimidine-4-carboxylic acid are obtained.

$^1$H NMR spectrum (300 MHz, $(CD_3)_2SO$ d6, δ in ppm): 2.65 (s: 3H); 2.79 (s: 3H); 2.85 (s: 3H); 3.47 (s: 6H); 4.27 (s: 3H); 6.87 (broad s: 1H); 7.33 (s: 1H); 7.47 (broad s: 1H); 7.89 (d, J=9 Hz: 1H); 8.04 (dd, J=9 and 2 Hz: 1H); 8.12 (d, J=9 Hz: 1H); 8.34 (dd, J=9 and 2 Hz: 1H); 8.93 (d, J=2 Hz: 1H); 9.18 (d, J=2 Hz: 1H); 10.81 (broad s: 1H); 10.84 (broad s: 1H); 13.93 (unresolved complex: 1H).

EXAMPLE 14

Preparation of the (4-dimethylamino-2-methylquinolin-6-ylamino)amide of 6-(4-amino-2-methylquinolin-6-ylamino)-2-methylsulfanylpyrimidine-4-carboxylic acid

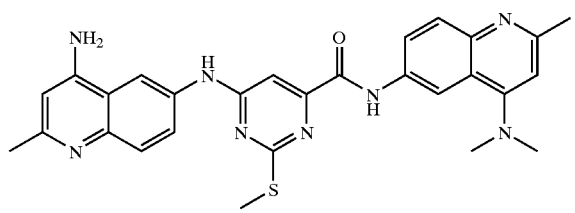

The title compound is prepared by following the procedures of Example 12 and by employing the following materials in amounts as specified:

Starting with 19 mg of 6-amino-4-amino-2-methylquinoline, 50 mg of (4-dimethylamino-2-methylquinolin-6-ylamino)amide of 6-chloro-2-methylsulfanylpyrimidine-4-carboxylic acid, 32 mg of sodium carbonate and 3 mL of dimethylformamide, 12 mg of (4-dimethylamino-2-methylquinolin-6-ylamino)amide of 6-(4-amino-2-methylquinolin-6-ylamino)-2-methylsulfanylpyrimidine-4-carboxylic acid are obtained.

$^1$H NMR spectrum (300 MHz, (CD$_3$)$_2$SO d6, δ in ppm): 2.66–2.77–2.81 and 2.82 (4 s: 9H in total); 3.47 (s: 6H); 6.90 (broad s: 1H); 7.37 (broad s: 1H); 7.70 (unresolved complex: 1H); 7.92 (d, J=9 Hz: 1H); 8.15 (mt: 2H); 8.35 (dd, J=9 and 1.5 Hz: 1H); 8.81 (unresolved complex: 1H); 8.96 (d, J=1.5 Hz: 1H); 10.79 (unresolved complex: 1H); 10.81 (broad s: 1H) 13.99 (unresolved complex: 1H).

EXAMPLE 15

Preparation of (4-dimethylamino-2-methylquinolin-6-ylamino)amide of 6-(4-amino-2-methylquinolin-6-ylamino)-2-methylsulfanylpyrimidine-4-carboxylic acid

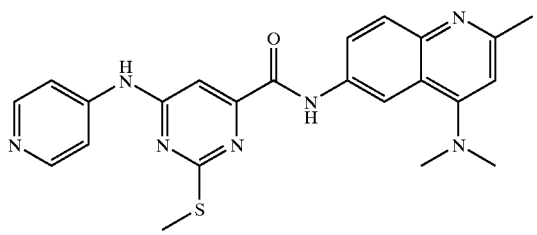

The title compound is prepared by following the procedures of Example 12 and by employing the following materials in amounts as specified: Starting with 9.4 mg of 4-aminopyridine, 50 mg of (4-dimethylamino-2-methylquinolin-6-ylamino)amide of 6-chloro-2-methylsulfanylpyrimidine-4-carboxylic acid, 32 mg of sodium carbonate and 3 mL of dimethylformamide, 9 mg of (4-dimethylamino-2-methylquinolin-6-ylamino)amide of 2-methylsulfanyl-6-(pyridin-4-ylamino)-pyrimidine-4-carboxylic acid are obtained.

$^1$H NMR spectrum (400 MHz, (CD$_3$)$_2$SO d6, at a temperature of 373K, δ in ppm): 2.69 (s: 3H); 2.74 (s: 3H); 3.48 (s: 6H); 6.88 (s: 1H); 7.37 (s: 1H); 7.79 (broad d, J=5.5 Hz: 2H); 7.92 (d, J=9 Hz: 1H); 8.29 (dd, J=9 and 2 Hz: 1H); 8.53 (broad d, J=5.5 Hz: 2H); 8.94 (d, J=2 Hz: 1H); 10.29 (unresolved complex: 1H); 10.56 (broad s: 1H).

EXAMPLE 16

Preparation of N,N'-bis(4-amino-2-methyl-6-quinolyl)-2,4-diamino-6-chloro-5-methylsulfanylpyrimidine

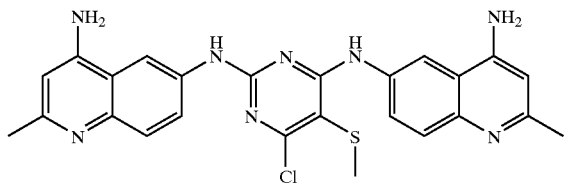

A mixture of 43 mg of N-(4-amino-2-methyl-6-quinolyl)-2-amino-4,6-dichloro-5-methylsulfanylpyrimidine and 55 mg of 4,6-diamino-2-methylquinoline in 5 mL of ethanol is heated under reflux for about 3 hours, left at a temperature in the region of 20° C. for about 16 hours and then filtered. The filtrate is concentrated under reduced pressure (2.7 kPa) at a temperature in the region of 40° C., and then the residue obtained is purified by HPLC (column: C18 Waters, 5 M, 50×19 mm; eluent: elution gradient water-acetonitrile-TFA (0.07%) from 95-5 to 5-95 over 30 minutes). The fractions containing the desired product are combined and concentrated to dryness under reduced pressure (2.7 kPa) at a temperature in the region of 40° C. to obtain 12 mg of N,N'-bis(4-amino-2-methyl-6-quinolyl)-2,4-diamino-6-chloro-5-methylsulfanyl-pyrimidine in the form of a beige colored solid.

$^1$H NMR spectrum (400 MHz, (CD$_3$)$_2$SO d6, at a temperature of 353K, δ in ppm): 2.40 (s: 3H); 2.61 (s: 3H); 2.63 (s: 3H); 6.52 (s: 1H); 6.54 (s: 1H); 7.68 (d, J=9 Hz: 1H); 7.72 (d, J=9 Hz: 1H); 7.98 (broad d, J=9 Hz: 1H); 7.99 (unresolved complex: 2H); 8.18 (unresolved complex: 2H); 8.23 (dd, J=9 and 1.5 Hz: 1H); 8.29 (broad s: 1H); 8.45 (broad s: 1H); 9.25 (broad s: 1H); 9.88 (broad s: 1H); 13.23 (broad unresolved complex: 1H).

N,N-(4-Amino-2-methyl-6-quinolyl)-2-amino-4,6-dichloro-5-methylsulfanylpyrimidine may be prepared by carrying out the procedure as set forth above in the following manner:

1.1 g of 4,6-diamino-2-methylquinoline are added in portions to a solution of 1 g of 2,4,6-trichloro-5-methylsulfanylpyrimidine and 6 mL of 2-butanone, at a temperature in the region of 0° C., followed at a temperature in the region of 20° C. by 0.434 mL of 30% sodium hydroxide. After stirring for 3 hours at a temperature in the region of 20° C., the reaction medium is filtered, the solid residue is rinsed with 2-butanone, with acetone and then air-dried. 875 mg of a beige powder are thus obtained, which powder is purified by flash chromatography on a silica gel column (Flashpack, 50 g of silica, particle size 0.015–0.035 mm), eluting with a dichloromethane-2N ammoniacal methanol (95-5 by volume) mixture. The fractions containing the desired product are combined and concentrated to dryness under reduced pressure (2.7 kPa) at a temperature in the region of 40° C. 80 mg of N-N-(4-amino-2-methyl-6-quinolyl)-2-amino-4,6-dichloro-5-methylsulfanylpyrimidine are obtained in the form of an off-white solid.

2,4,6-Trichloro-5-methylsulfanyl-pyrimidine may be prepared as described in: Mattioda, Georges; Obellianne, Pierre; Gauthier, Henri; Loiseau, Gerard; Millischer, Rene; Donadieu, Anne M.; Mestre, Michel. Synthesis and pharmacological properties of 4-piperazino-5-methylthiopyrimidines. Selection of new antiemetic agents. J. Med. Chem. (1975), 18(6), 553–9.

EXAMPLE 17

Preparation of bis[(4-amino-2-methylquinolin-6-yl)amido]-2,5-pyridinedicarboxylic acid Hydrochloride

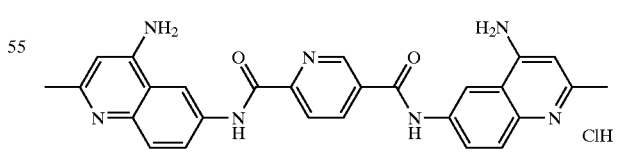

4-(4,6-Dimethoxy-1,3,5-triazine-2-yl)-4-methylmorpholinium chloride (183 mg) are added to a solution of 50 mg (0.29 mmol) of 2,5-pyridinedicarboxylic acid and of 114 mg (0.66 mmol) of 2-methylquinoline-4,6-diamine in 5 mL of dimethylformamide, at a temperature in the region of 20° C. The mixture obtained is stirred at a temperature in the region of 20° C. for about 12 hours. The reaction mixture is successively taken up in 2 mL of acetonitrile and 2 mL of diisopropyl ether, the precipitate thus obtained is slowly filtered on a 6 mL BOND-ELUT cartridge filled with sintered material. The insoluble matter obtained is washed with 3 mL of diisopropyl ether and then dried under vacuum at a temperature in the region of 20° C. for 2 hours. 134 mg of bis[(4-amino-2-methylquinolin-6-yl)amido]-2,5-pyridinedicarboxylic acid are thus obtained in the form of a yellow powder whose characteristics are the following:

$^1$H NMR spectrum (300 MHz, (CD$_3$)$_2$SO d6, δ in ppm): 2.59 (s: 6H); 6.62 (s: 2H); 7.92 and 7.95 (2 d, J=9 Hz: 2H); 8.10 (dd, J=9 and 1.5 Hz: 1H); 8.32 (dd, J=9 and 1.5 Hz: 1H); 8.40 (d, J=8.5 Hz: 1H); 8.50 (unresolved complex: 4H); 8.71 (dd, J=8.5 and 2 Hz: 1H); 8.78 and 8.80 (2 broad s: 2H); 9.37 (d, J=2 Hz: 1H); 11.10 (s: 1H); 11.22 (s: 1H).

EXAMPLE 18

Preparation of N,N'-bis(4-dimethylamino-2-methylquinolin-6-yl)but-2-enediamide

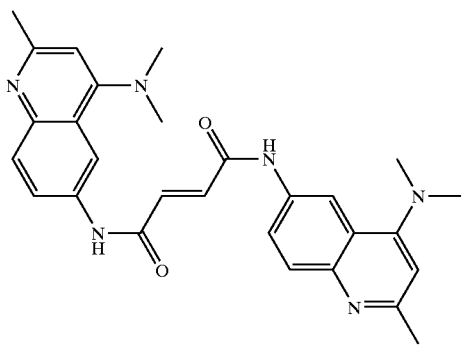

4-(4,6-Dimethoxy-1,3,5-triazine-2-yl)-4-methylmorpholinium chloride (61 mg, 0.22 mmol) and then 44.3 mg (0.22 mmol) of 4-dimethylamino-6-amino-quinaldine are successively added to a solution of 11.6 mg (0.1 mmol) of fumaric acid in 2 mL of dimethylformamide, at a temperature in the region of 20° C. The mixture obtained is stirred at a temperature in the region of 20° C. for about 19 hours. The reaction mixture is filtered on sintered glass with a No. 3 porosity, and then washed with 2 mL of diisopropyl ether. The crude material thus obtained is solubilized in a (dichloromethane/2M ammoniacal methanol) (90-10 by volume) mixture and then deposited on a 20×20 MERCK preparative plate with the reference 1.05744 having a thickness of 0.5 mm. After elution in the (dichloromethane/2M ammoniacal methanol) (90-10 by volume) mixture, the product is isolated by taking up the silica with a (dichloromethane/methanol) (80-20 by volume) mixture.

The filtrate is concentrated to dryness under reduced pressure (2.7 kPa) at 40° C.; 19 mg of N,N'-bis(4-dimethylamino-2-methylquinolin-6-yl)but-2-enediamide are thus obtained in the form of an orange-colored solid whose characteristics are the following:

$^1$H NMR spectrum (400 MHz, (CD$_3$)$_2$SO d6, δ in ppm): 2.56 (s: 6H); 3.00 (s: 12H); 6.81 (s: 2H); 7.31 (s: 2H); 7.82 (d, J=9 Hz: 2H); 7.85 (dd, J=9 and 1.5 Hz: 2H); 8.61 (broad s: 2H); 10.79 (broad s: 2H).

EXAMPLE 19

Preparation of bis[(4-dimethylamino-2-methylquinolin-6-yl)-amido]-2,5-pyridinedicarboxylic acid

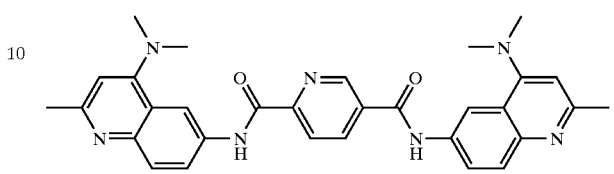

4-(4,6-Dimethoxy-1,3,5-triazine-2-yl)-4-methyl-morpholinium chloride (183 mg, 0.66 mmol) and then 133 mg (0.66 mmol) of 4-dimethylamino-6-aminoquinaldine are successively added to a solution of 50 mg (0.29 mmol) 2,5-pyridinedicarboxylic acid in 5 mL of dimethylformamide, at a temperature in the region of 20° C. 2.5 mL of dimethylformamide are added after stirring for 1 hour at a temperature in the region of 20° C. The mixture obtained is stirred at a temperature in the region of 20° C. for about 20 hours. The reaction mixture is taken up in 2 mL of diisopropyl ether, filtered on sintered glass and then washed with 2×2 mL of diisopropyl ether. The insoluble matter obtained is dried under vacuum at a temperature in the region of 20° C. for about 2 hours. 157 mg bis-[(4-dimethylamino-2-methylquinolin-6-yl)-amido]-2,5-pyridinedicarboxylic acid are thus obtained in the form of a yellow solid whose characteristics are the following:

$^1$H NMR spectrum (300 MHz, (CD$_3$)$_2$SO d6, δ in ppm): 2.67 (s: 6H); 3.42 and 3.44 (2 broad s: 12H); 6.90 and 6.92 (2 s: 2H); of 7.90 to 8.05 (mt: 2H); 8.25 (broad d, J=9 Hz: 1H); 8.41 (d, J=8.5 Hz: 1H); 8.46 (broad d, J=9 Hz: 1H); 8.70 (dd, J=8.5 and 2 Hz: 1H); 9.00 and 9.06 (2 broad s: 2H); 9.34 (broad s: 1H); 11.25 (broad s: 1H); 11.42 (broad s: 1H); 13.56 (unresolved complex: 2H).

EXAMPLE 20

Preparation of bis[(4-dimethylamino-2-methylquinolin-6-yl)-amido]-2,4-pyridinedicarboxylic acid

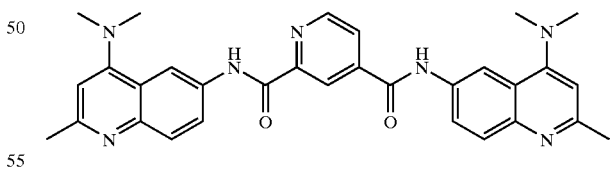

4-(4,6-Dimethoxy-1,3,5-triazine-2-yl)-4-methylmorpholinium chloride (183 mg, 0.66 mmol) and then 133 mg (0.66 mmol) of 4-dimethylamino-6-amino-quinaldine are successively added to a solution of 50 mg (0.3 mmol) of 2,4-pyridinedicarboxylic acid in 3 mL of dimethylformamide, at a temperature in the region of 20° C. The mixture obtained is stirred at a temperature in the region of 20° C. for about 17 hours.

The reaction mixture is taken up in 20 mL of diisopropyl ether, filtered on sintered glass and then washed with 2×10 mL of diisopropyl ether. The crude material thus obtained is solubilized in a (dichloromethane/2M ammoniacal methanol) (90-10 by volume) mixture and then deposited on four 20×20 MERCK preparative plates with the reference 1.05744 having a thickness of 0.5 mm. After elution with (dichloromethane/2M ammoniacal methanol) (90-10 by volume) mixture, the product is isolated by taking up the silica in a (dichloromethane/methanol) (80-20 by volume) mixture.

The filtrate is concentrated to dryness under reduced pressure (2.7 kPa) at 40° C.; 66 mg of bis[(4-dimethylamino-2-methylquinolin-6-yl)-amido]-2,4-pyridinedicarboxylic acid are thus obtained in the form of a bright yellow solid whose characteristics are the following:

$^1$H NMR spectrum (300 MHz, (CD$_3$)$_2$SO d6, δ in ppm): 2.59 and 2.60 (2 s: 6H); 3.01 and 3.03 (2 s: 12H); 6.82 and 6.84 (2 s: 2H); 7.84 and 7.86 (2 d, J=9 Hz: 2H); 8.04 (dd, J=9 and 2.5 Hz: 1H); 8.14 (dd, J=9 and 2.5 Hz: 1H); 8.23 (dd, J=6.5 and 1.5 Hz: 1H); 8.66 (d, J=2.5 Hz: 1H); 8.80 (broad s: 1H); 8.93 (d, J=2.5 Hz: 1H); 9.02 (d, J=6.5 Hz: 1H); 10.99 (s: 1H); 11.09 (s: 1H).

EXAMPLE 21

Preparation of N,N'-bis(4-dimethylamino-2-methylquinolin-6-yl)-1,4-phenylenediacetamide

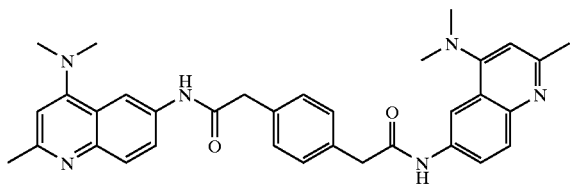

4-(4,6-Dimethoxy-1,3,5-triazine-2-yl)-4-methylmorpholinium chloride (91.3 mg, 0.33 mmol) and then 66.4 mg (0.33 mmol) of 4-dimethylamino-6-amino-quinaldine are successively added to a solution of 29.1 mg (0.15 mmol) of 1,4-phenylenediacetic acid in 2 mL of dimethylformamide, at a temperature in the region of 20° C. The mixture obtained is stirred at a temperature in the region of 20° C. for about 18 hours.

The reaction mixture is concentrated to dryness under reduced pressure (2.7 kPa) at 40° C. The residue obtained is taken up in 5 mL of toluene and then concentrated to dryness under reduced pressure (2.7 kPa) at 40° C. The yellowish solid thus obtained is purified by FLASH chromatography on a BOND-ELUT cartridge (27 mm in diameter) filled with 25 g of conditioned silica (15–35 μm) and then eluted with a (dichloromethane/2M ammoniacal methanol) (90-10 by volume) mixture at a flow rate of 10 mL per minute. The fractions between 180 and 250 mL are combined and concentrated to dryness under reduced pressure (2.7 kPa) to 40° C. 40 mg of N,N'-bis-(4-dimethylamino-2-methylquinolin-6-yl)-1,4-phenylenediacetamide are thus obtained in the form of a foam whose characteristics are the following:

$^1$H NMR spectrum (300 MHz, (CD$_3$)$_2$SO d6, δ in ppm): 2.51 (s: 6H); 2.93 (s: 12H); 3.69 (s: 4H); 6.76 (s: 2H); 7.04 (s: 4H); 7.71 (dd, J=9 and 2.5 Hz: 2H); 7.77 (d, J=9 Hz: 2H); 8.49 (d, J=2.5 Hz: 2H); 10.40 (broad s: 2H).

EXAMPLE 22

Preparation of [(4-dimethylamino-2-methylquinolin-6-yl)-amido]-5-[(4-dimethylamino-2-methylquinolin-6-ylamino)methyl]pyridine-2-carboxylic acid Hydrochloride

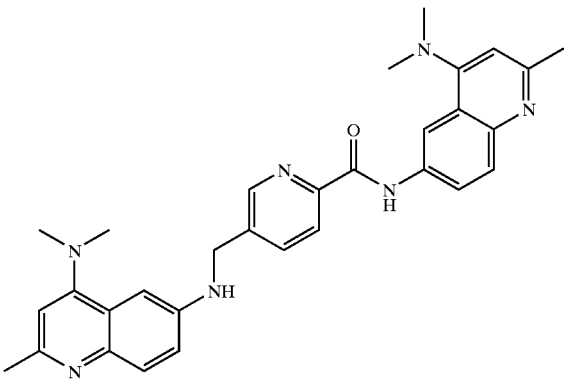

Ethyl azodicarboxylate (63 μl, 0.4 mmol) are added to a solution of 75 mg (0.22 mmol) of [(dimethylamino-4-methyl-2-quinolin-6-yl)-amido]-5-hydroxymethylpyridine-2-carboxylic acid (prepared as indicated below in a)), 89 mg (0.44 mmol) of 4-dimethylamino-6-amino-quinaldine and 175 mg (0.67 mmol) of triphenylphosphine in 5 mL of dichloromethane stabilized over amylene, purged with argon, at a temperature in the region of 20° C. The mixture obtained is stirred at a temperature in the region of 20° C. for about 15 hours. The reaction mixture is deposited on a BOND-ELUT VARIAN cartridge with the reference 1225-6054 containing 3 g of SCX phase conditioned in dichloromethane. The cartridge is successively washed with dichloromethane (10 mL) and methanol (10 mL) before being eluted with 2M ammoniacal methanol. The ammoniacal fractions are concentrated to dryness under reduced pressure (2.7 kPa) at a temperature in the region of 40° C. 179 mg of crude material are thus obtained. 46 mg of the preceding crude material are taken up in a normal hydrochloric acid solution (338 μl), the solution thus obtained is deposited on a Flash cartridge 16 mm in diameter containing 2.5 g of Waters OASIS phase with the reference WAT020585 conditioned in methanol and then in water. Elution is performed using an elution gradient in a methanol/water system passing from 100% water to 100% methanol over 40 minutes at a flow rate of 10 mL per minute and a collection of 0.5 minutes per tube. Fractions 75 to 80 are combined and concentrated to dryness under reduced pressure (2.7 kPa) at 40° C. 4 mg of [(4-dimethylamino-2-methylquinolin-6-yl)-amido]-5-[(4-dimethylamino-2-methylquinolin-6-ylamino)-methyl]-pyridine-2-carboxylic acid hydrochloride are thus obtained in the form of a brown solid whose characteristics are the following:

$^1$H NMR spectrum (400 MHz, (CD$_3$)$_2$SO d6, at a temperature of 353 K, δ in ppm): 2.50 (s: 3H); 2.57 (s: 3H); 2.79 (s: 6H); 3.03 (s: 6H); 4.60 (d, J=6 Hz: 2H); 6.42 (t, J=6 Hz: 1H); 6.66 (s: 1H); 6.77 (s: 1H); 6.86 (d, J=2.5 Hz: 1H); 7.21 (dd, J=9 and 2.5 Hz: 1H); 7.63 (d, J=9 Hz: 1H); 7.81 (d, J=8 Hz: 1H); 8.01 (dd, J=10 and 2.5 Hz: 1H); 8.08 (very broad d, J=10 Hz: 1H); 8.17 (d, J=8 Hz: 1H); 8.69 (d, J=2.5 Hz: 1H); 8.81 (broad s: 1H); 10.57 (broad s: 1H).

a) Preparation of [(dimethylamino-4-methyl-2-quinolin-6-yl)-amido]-5-hydroxymethylpyridine-2-carboxylic acid

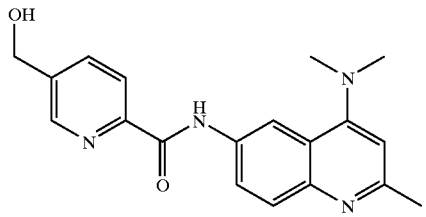

275 µl (0.55 mmol) of a 2M lithium borohydride solution in tetrahydrofuran are added to a solution of 200 mg (0.549 mmol) of [(4-dimethylamino-2-methylquinolin-6-yl)-amido]-5-(methoxycarbonyl)pyridine-2-carboxylic acid (prepared as indicated below in b)) in 2 mL of tetrahydrofuran, under an argon atmosphere, at a temperature in the region of 20° C. The mixture obtained is stirred at a temperature in the region of 20° C. for about 15 hours.

The reaction medium is taken up in a saturated ammonium chloride solution and then extracted with 10 mL of ethyl acetate. The organic phase is dried with magnesium sulfate and then concentrated under reduced pressure (2.7 kPa). 170 mg of [(dimethylamino-4-methyl-2-quinolin-6-yl)amido]-5-hydroxymethylpyridine-2-carboxylic acid are thus obtained in the form of an oil whose characteristics are the following:

$^1$H NMR spectrum (300 MHz, (CD$_3$)$_2$SO d6, δ in ppm): 2.57 (s: 3H); 3.02 (s: 6H); 4.71 (d, J=6 Hz: 2H); 5.53 (t, J=6 Hz: 1H); 6.80 (s: 1H); 7.81 (d, J=9 Hz: 1H); 8.02 (dd, J=8 and 2 Hz: 1H); 8.10 (dd, J=9 and 2.5 Hz 1H); 8.20 (d, J=8 Hz: 1H); 8.73 (d, J=2 Hz: 1H); 8.78 (d, J=2.5 Hz: 1H); 10.91 (s: 1H).

b) Preparation of [(4-dimethylamino-2-methylquinolin-6-yl)amido]-5-(methoxycarbonyl)pyridine-2-carboxylic acid

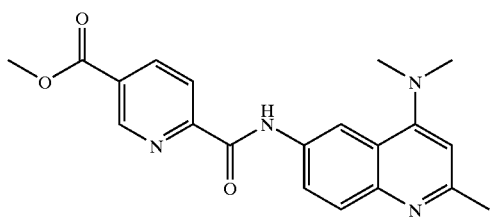

Diisopropylcarbodiimide (674 µl, 4.33 mmol) and 486 mg (3.6 mmol) of hydroxybenzotriazole are successively added to a solution of 452 mg (2.5 mmol) of 5-(methoxycarbonyl)pyridine-2-carboxylic acid and 503 mg (2.5 mmol) of 4-dimethylamino-6-amino-quinaldine in 10 mL of dimethylformamide, under an inert argon atmosphere, at a temperature in the region of 20° C. The solution obtained is stirred at a temperature in the region of 20° C. for about 15 hours.

The reaction mixture is deposited on a MEGA BOND ELUT VARIAN cartridge with the reference 1225-6065 containing 20 g of SCX phase conditioned in dimethylformamide. The cartridge is successively washed with dimethylformamide (30 mL) and with methanol (30 mL) before being eluted with 2M ammoniacal methanol. The ammoniacal fractions are concentrated to dryness under reduced pressure (2.7 kPa) at a temperature in the region of 40° C.

400 mg of [(4-dimethylamino-2-methylquinolin-6-yl)amido]-5-(methoxycarbonyl)pyridine-2-carboxylic acid are thus obtained in the form of brown insoluble matter.

TLC analysis Merck 60 F$_{254}$: 0.31 in (dichloromethane/methanol) (9/1) (V/V)

EXAMPLE 23

Preparation of bis[(4-amino-2-methylquinolin-6-yl)-amido]-2,6-pyridinedicarboxylic acid hydrochloride

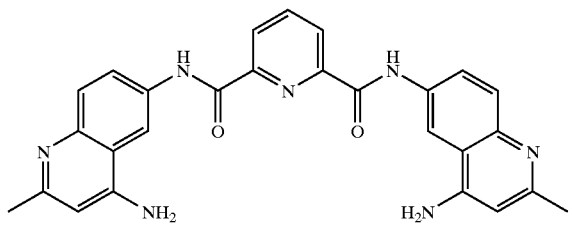

4-(4,6-Dimethoxy-1,3,5-triazine-2-yl)-4-methylmorpholinium chloride (91 mg, 0.33 mmol) are added to a solution of 25 mg (0.15 mmol) of 2,6-pyridine dicarboxylic acid and 57 mg (0.33 mmol) of 2-methylquinoline-4,6-diamine in 3 mL of dimethylformamide, at a temperature in the region of 20° C. The mixture obtained is stirred at a temperature in the region of 20° C. for about 15 hours. The reaction mixture is successively taken up in 2 mL of acetonitrile and 2 mL of diisopropyl ether, the precipitate thus obtained is slowly filtered on a 6 mL BOND-ELUT cartridge filled with sintered material. The insoluble matter obtained is washed with 1 mL of ethanol, taken up in 2 mL of diisopropyl ether and then dried under vacuum at a temperature in the region of 20° C. for 2 hours. 47 mg of bis[(4-amino-2-methylquinolin-6-yl)-amido]-2,6-pyridinedicarboxylic acid hydrochloride are thus obtained in the form of a gray powder whose characteristics are the following:

$^1$H NMR spectrum (300 MHz, (CD$_3$)$_2$SO d6, δ in ppm): 2.63 (s: 6H); 6.65 (s: 2H); 8.01 (d, J=9 Hz: 2H); 8.39 (dd, J=9 and 7 Hz: 1H); from 8.40 to 8.55 (mt: 4H); 8.74 (unresolved complex: 4H); 8.94 (broad s: 2H); 11.70 (s: 2H); from 13.30 to 14.50 (broad unresolved complex: 1H).

EXAMPLE 24

Preparation of bis-[(4-dimethylamino-2-methylquinolin-6-yl)-amido]-2,6-pyridinedicarboxylic acid hydrochloride

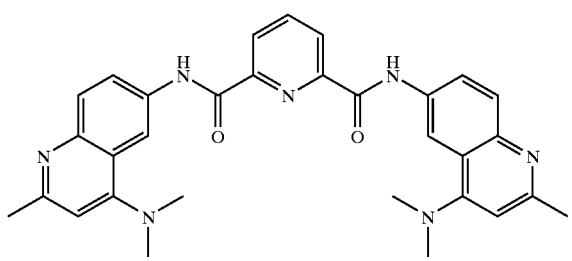

4-(4,6-Dimethoxy-1,3,5-triazine-2-yl)-4-methylmorpholinium chloride (91 mg, 0.33 mmol) are added to a solution of 25 mg (0.15 mmol) of 2,6-pyridinedicarboxylic acid and of 66 mg (0.33 mmol) of 4-dimethylamino-6-aminoquinaldine in 3 mL of dimethylformamide, at a temperature in the region of 20° C. The mixture obtained is stirred at a temperature in the region of 20° C. for about 15 hours. The reaction mixture is taken up in 3 mL of acetonitrile and the precipitate thus obtained is slowly filtered on a 6 mL BOND-ELUT cartridge filled with sintered material. The insoluble matter obtained is washed with 3 mL of diisopropyl ether and then dried under vacuum at a temperature in the region of 40° C. for 2 hours. 74 mg of bis[(4-dimethylaminoamino-2-methylquinolin-6-yl)amido]-2,6-pyridinedicarboxylic acid hydrochloride are thus obtained in the form of a dark solid whose characteristics are the following:

$^1$H NMR spectrum (300 MHz, $(CD_3)_2SO$ d6, δ in ppm): 2.67 (s: 6H); 3.48 (broad s: 12H); 6.91 (s: 2H); 7.98 (mt: 2H); 8.36 (dd, J=9 and 7 Hz: 1H); 8.47 (mt: 2H); 8.54 (very broad d, J=9 Hz: 2H); 9.25 (broad s: 2H); 11.88 (very broad s: 2H); from 13.50 to 14.30 (broad unresolved complex: 1H).

EXAMPLE 25

The G-quartet, antitelomerase and cytotoxic activities of the various compounds exemplified are determined according to the operating protocols described above.

The table which follows gives the biological results obtained according to the protocols indicated above for the products of the present application.

| Example | G4 Tm (G4 stabilization differential in ° C., product tested at 1 mM) | Inhibition of telomerase TRAP test (IC50, μM) |
|---|---|---|
| 1 | 2.5 | 1.7 |
| 2 | 10.5 | 0.9 |
| 3 | 1.7 | 0.95 |
| 6 | 16 | 0.31 |
| 7 | 2 | 1.5 |
| 8 | 2.5 | 0.75 |
| 9 | 11.5 | 0.8 |
| 16 | 5 | 0.55 |
| 17 | 5.5 | 0.3 |
| 18 | 9 | 1.2 |
| 19 | 16 | 0.6 |
| 20 | nt | 1.1 |
| 21 | 3 | 1.3 |
| 22 | 4 | 2.9 |
| 23 | 23 | 0.2 |
| 24 | 15.6 | 0.5 |

What is claimed is:

1. A compound corresponding to the following formula:

nitrogen-containing aromatic ring —(NR$_3$)p-(CO)n-distribution agent —(CO)m-(NR'$_3$)q- aromatic or non-aromatic ring wherein
n, m, p and q are 1; and wherein
the nitrogen-containing aromatic ring is:
a quinoline optionally substituted with at least one group N(Ra)(Rb) in which Ra and Rb, are identical or different, and are independently of each other hydrogen or a C1–C4 alkyl; or one C1–C4 alkyl or alkoxy;
a quinoilne possessing a nitrogen atom in quaternary form; or
a pyridine;
the aromatic or non-aromatic ring is;
a quinoline optionally substituted with at least one group N(Ra)(Rb) in which Ra and Rb, are identical or different, and are independently hydrogen or a C1–C4 alkyl; or
one C1–C4 alkyl or alkoxy;
a quino line possessing a nitrogen atom in quaternary form;
a pyridine; or
a phenyl optionally substituted with halogen, C1–C4 alkoxy, cyano, carbonylamino optionally substituted with one or more C1–C4 alkyl, guanyl, C1–C4 alkylthio, amino, C1–C4 alkylamino, C1–C4 dialkylamino, nitro, C1–C4 alkyleneamino or C2–C4 alkenyleneamino;
R$_3$ and R'$_3$, which are identical or different, represent independently of each other hydrogen or C1–C4 alkyl;
the distribution agent is:
a triazine group optionally substituted with one or more radicals chosen from halogen, C1–C4 alkyl, and thio, oxy or amino which are themselves optionally substituted with one or more C1–C4 alkyl;
a 5- or 6-membered heterocyclic radical containing a sulfur, oxygen or nitrogen atom;
a phenyl; or
a diazine group; and wherein
the heterocyclic, phenyl and diazine are optionally substituted with the same groups as the triazine;
or an isomer, an enantiomer, a diastereoisomer or a mixture thereof, or a pharmaceutically acceptable salt thereof;
with the proviso that:
when the distribution agent is 2,5-pyridyl, 2,6-pyridyl, 2,5-furanyl or phenyl unsubstituted or substituted with NH$_2$ or 2-chloro, and R$_3$ and R'$_3$ are hydrogen, then the nitrogen-containing aromatic ring and the aromatic ring are not both quinoline which is unsubstituted or substituted with C1–C4 alkyl.

2. The compound according to claim 1 which binds the G-quadruplex structure of telomeres.

3. The compound according to claim 1 wherein the distribution agent is chosen from the heterocyclic group, phenyl, and diazine.

4. The compound according to claim 1 wherein the distribution agent is thienyl or pyridyl.

5. The compound according to claim 1 wherein the distribution agent is chosen from thienyl, pyridyl, phenyl, and diazine.

6. The compound according to claim 1 wherein the diazine group is a pyrimidine.

7. The compound according to claim 1 having the following formula (IA):

$$\left[O \underset{n}{\overset{\|}{\diagup}} A \underset{m}{\overset{\|}{\diagdown}} O\right] \quad (IA)$$
$$(NR_3)p \quad (NR_3')q$$
$$| \qquad |$$
$$Ar_1 \qquad Ar_2$$

wherein
n, m, p and q are 1;
A represents:
a 5- to 6-membered heterocyclic radical containing a sulfur, oxygen or nitrogen atom;

a phenyl or a diazine group; and wherein the heterocyclic, phenyl and diazine are optionally substituted with one or more radicals chosen from halogen, C1–C4 alkyl, and thio, oxy or amino which are themselves optionally substituted with one or more C1–C4 alkyl;

$R_3$ and $R'_3$, which are identical or different, represent independently of each other hydrogen or C1–C4 alkyl;

$Ar_1$ and $Ar_2$, which are identical or different, and are independently of each other selected from:

a quinoline optionally substituted with at least a group N(Ra)(Rb) in which Ra and Rb are identical or different and are independently of each other hydrogen or a C1–C4 alkyl; or a C1–C4 alkyl or alkoxy;

a quinoline possessing a nitrogen atom in quaternary form;

a pyridine optionally attached at the 4-position or fused with an aryl or heteroaryl group, optionally substituted with a C1–C4alkyl; or a phenyl optionally substituted with halogen, C1–C4 alkoxy, cyano, carbonylamino optionally substituted with one or more C1–C4 alkyl, guanyl, C1–C4 alkylthio, amino, C1–C4 alkylamino, C1–C4 dialkylamino, nitro, C1–C4 alkyleneamino or C2–C4 alkenyleneamino;

or an isomer, an enantiomer, a diastereoisomer or a mixture thereof, or a pharmaceutically acceptable salt thereof;

with the proviso that:

when A is 2,5-pyridyl, 2,6-pyridyl, 2,5-furanyl or phenyl unsubstituted or substituted with $NH_2$ or 2-chloro, and when $R_3$ and $R'_3$ are hydrogen, then $Ar_1$ and $Ar_2$ are not both quinoline which is unsubstituted or substituted with C1–C4 alkyl.

8. The compound according to claim 11 wherein A is chosen from heterocyclic group, phenyl and pyrimidine.

9. The compound according to claim 7 wherein the diazine group which A may represent is pyrimidine.

10. The compound according to claim 1 having the following formula (I):

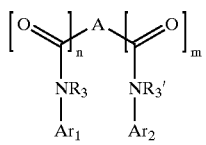

(I)

wherein n and m are 1;

A represents:

a 5- to 6-membered heterocyclic radical containing a sulfur, oxygen or nitrogen atom;

a phenyl; or a diazine group; and wherein the heterocyclic, phenyl and diazine are optionally substituted with one or more radicals chosen from halogen, C1–C4 alkyl, and thio, oxy or amino which are themselves optionally substituted with one or more C1–C4 alkyl;

$R_3$ and $R'_3$, which are identical or different, represent independently of each other hydrogen or C1–C4 alkyl;

$Ar_1$ and $Ar_2$, which are identical or different, and are independently of each other selected from:

a quinoline optionally substituted with at least a group N(Ra)(Rb) in which Ra and Rb are identical or different, and are independently of each other hydrogen or a C1–C4 alkyl; or a C1–C4 alkyl or alkoxy;

a quinoline possessing a nitrogen atom in quaternary form;

a pyridine optionally attached at the 4-position or fused with an aryl or heteroaryl group, optionally substituted with a C1–C4 alkyl; or a phenyl optionally substituted with halogen, C1–C4 alkoxy, cyano, carbonylamino optionally substituted with one or more C1–C4 alkyl, guanyl, C1–C4 alkylthio, amino, C1–C4 alkylamino, C1–C4 dialkylamino, nitro, C1–C4 alkyleneamino or C2–C4 alkenyleneamino;

or an isomer, an enantiomer, a diastereoisomer or a mixture thereof, or a pharmaceutically acceptable salt thereof;

with the proviso that:

when A is 2,5-pyridyl, 2,6-pyridyl, 2,5-furanyl or phenyl unsubstituted or substituted with $NH_2$ or 2-chloro, and when $R_3$ and $R_3'$ are hydrogen, then $Ar_1$ and $Ar_2$ are not both quinoline which is unsubstituted or substituted with C1–C4 alkyl.

11. The compound according to claim 10 wherein A is chosen from thienyl, pyridyl, phenyl and pyrimidine.

12. The compound according to claim 10 wherein $Ar_1$ and $Ar_2$ represent:

a quinoline optionally substituted with at least a group N(Ra)(Rb) in which Ra and Rb are identical or different, and are independently of each other hydrogen or C1–C4 alkyl; or a C1–C4 alkyl or alkoxy a quinoline possessing a nitrogen atom in quaternary form; or pyridine.

13. The compound according to claim 10 wherein $Ar_1$ and $Ar_2$ are chosen from the following groups: 4-amino-, 4-methylamino-, 4-dimethylamino- or 4-alkoxy-quinolyl or -quinolinium in which the quinolinium is optionally substituted with one or two methyl groups.

14. The compound according to claim 10 wherein A is optionally substituted with one or more radicals chosen from halogen, C1–C4 thioalkyl, amino, C1–C4 alkylamino or C1–C4 dialkylamino.

15. The compound according to claim 10 wherein A is optionally substituted with methylthio or halogen.

16. The compound of formula (IA) according to claim 11 wherein:

A represents:

thienyl or pyridyl;

pheny; or pyrimidyl optionally substituted with one or more radicals chosen from halogen or C1–C4 alkylthio;

$R_3$ and $R'_3$, which are identical or different, represent independently of each other hydrogen or C1–C4 alkyl;

$Ar_1$ and $Ar_2$, which are identical or different, and are independently of each other selected from:

a quinoline optionally substituted with at least a group N(Ra)(Rb) in which Ra and Rb are identical or different, and are independently of each other hydrogen or C1–C4 alkyl; or a C1–C4 alkyl or alkoxy;

a quinoline possessing a nitrogen atom in quaternary form; or a pyridyl;

or an isomer, an enantiomer, a diastereoisomer or a mixture thereof, or a pharmaceutically acceptable salt thereof.

17. The compound of formula (IA) according to claim 7 wherein:
A represents:
thienyl or pyridyl;
phenyl; or
pyrimidyl optionally substituted with one or more radicals chosen from halogen or C1–C4 alkylthio;

$R_3$ and $R'_3$, which are identical or different, represent independently of each other hydrogen or C1–C4 alkyl;

$Ar_1$ and $Ar_2$, which are identical or different, and are independently of each other selected from:
a quinoline optionally substituted with at least
a group N(Ra)(Rb) in which Ra and Rb, which are identical or different and are independently of each other hydrogen or C1–C4 alkyl; or
a C1–C4 alkyl or alkoxy;
a quinoline possessing a nitrogen atom in quaternary form; or
a pyridyl;

or an isomer, an enantiomer, a diastereoisomer or a mixture thereof, or a pharmaceutically acceptable salt thereof.

18. The compound according to claim 17 wherein $Ar_1$ and $Ar_2$, which are identical or different, and are independently of each other chosen from the 4-amino-, 4-methylamino-, 4-dimethylamino- or 4-alkoxy-quinolyl or -quinolinium groups in which the quinolinium is optionally substituted with one or two methyl groups.

19. The compound according to claim 17 wherein $R_3$ and $R_3'$ represent hydrogen.

20. The compound according to claim 17 wherein:
1. $Ar_1$ represents:
a quinoline substituted with at least
one group N(Ra)(Rb) In which Ra and Rb are identical or different, and are independently of each other hydrogen or C1–C4 alkyl; or
a C1–C4 alkyl or alkoxy;
a quinoline possessing a nitrogen atom in quaternary form; and
2. $Ar_2$ represents
a quinoline substituted with at least
one group N(Ra)(Rb) in which Ra and Rb are identical or different, and are independently of each other hydrogen or C1–C4 alkyl; or
a C1–C4 alkyl or alkoxy;
a quinoline possessing a nitrogen atom in quaternary form; or
a pyridyl;

or an isomer, an enantiomer, a diastereoisomer or a mixture thereof, or a pharmaceutically acceptable salt thereof.

21. The compound of formula (IA) according to claim 7 chosen from:
bis[(4-methoxy-2-methylquinolin-6-yl)-amido]-2,5-thiophenedicarboxylic acid;
bis[(4-dimethylamino-2-methylquinolin-6-yl)-amido]-2,5-thiophenedicarboxylic acid;
bis[(4-amino-2-methylquinolin-6-yl)-amido]-2,5-thiophenedicarboxylic acid;
N,N'-bis(4-amino-2-methylquinolin-6-yl)isophthalamide;
N,N'-bis(4-dimethylamino-2-methylquinolin-6-yl)terephthalamide;
bis[(4-amino-2-methyl-quinolin-6-yl)-amido]-2,5-pyridinedicarboxylic acid hydrochloride;
bis[(4-dimethylamino-2-methyl-quinolin-6-yl)-amido]-2,5-pyridinedicarboxylic acid;
bis[(4-dimethylamino-2-methylquinolin-6-yl)-amido]-2,4-pyridinedicarboxylic acid;
bis[(4-amino-2-methyl-quinolin-6-yl)-amido]-2,6-pyridinedicarboxylic acid hydrochloride;
bis[(4-amino-2-methyl-quinolin-6-yl)amido]-2,6-pyridine dicarboxylic acid;
bis[(4-dimethylamino-2-methylquinolin-6-yl)amido]-2,6-pyridinedicarboxylic acid hydrochloride; and
bis[(4-dimethylamino-2-methylquinolin-6-yl)-amido]-2,6-pyridinedicarboxylic acid;

or an isomer, an enantiomer, a diastereoisomer or a mixture thereof, or a pharmaceutically acceptable salt thereof.

22. The compound according to claim 21 chosen from:
bis[(4-dimethylamino-2-methylquinolin-6-yl)-amido]-2,5-thiophenedicarboxylic acid;
N,N'-bis-(4-amino-2-methylquinolin-6-yl)isophthalamide;
bis[(4-amino-2-methylquinolin-6-yl)-amido]-2,6-pyridinedicarboxylic acid hydrochloride;
bis[(4-amino-2-methylquinolin-6-yl)-amido]-2,5-pyridinedicarboxylic acid;
bis-[(4-dimethylamino-2-methylquinolin-6-yl)-amido]-2,5-pyridinedicarboxylic acid; and
bis[(4-dimethylamino-2-methylquinolin-6-yl)amido]-2,4-pyridinedicarboxylic acid;

or an isomer, an enantiomer, a diastereoisomer or a mixture thereof, or a pharmaceutically acceptable salt thereof.

23. A pharmaceutical composition comprising therapeutically effective amount of a compound of formula (I) in combination with a pharmaceutically acceptable carrier;

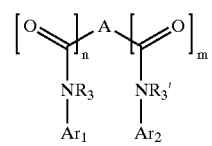

(I)

wherein
n and m are 1;
A represents:
a 5- to 6-membered heterocyclic radical containing a sulfur, oxygen or nitrogen atom;
a phenyl; or
a diazine group; and wherein
the heterocyclic, phenyl and diazine are optionally substituted with one or more radicals chosen from halogen, C1–C4 alkyl, and thio, oxy or amino which are themselves optionally substituted with one or more C1–C4 alkyl;
$R_3$ and $R'_3$, which are identical or different, represent independently of each other hydrogen or C1–C4 alkyl;
$Ar_1$ and $Ar_2$, which are identical or different, and are independently of each other selected from:
a quinoline optionally substituted with at least
a group N(Ra)(Rb) in which Ra and Rb are identical or different, and are independently of each other hydrogen or a C1–C4 alkyl; or
a C1–C4 alkyl or alkoxy;
a quinoline possessing a nitrogen atom in quaternary form;

a pyridine optionally attached at the 4-position or fused with an aryl or heteroaryl group, optionally substituted with a C1–C4 alkyl; or a phenyl optionally substituted with halogen, C1–C4 alkoxy, cyano, carbonylamino optionally substituted with one or more C1–C4 alkyl, guanyl, C1–C4 alkylthio, amino, C1–C4 alkylamino, C1–C4 dialkylamino, nitro, C1–C4 alkyleneamino or C2–C4 alkenyleneamino;

or an isomer, an enantiomer, a diastereoisomer or a mixture thereof, or a pharmaceutically acceptable salt thereof;
with the proviso that:
when A is 2,5-pyridyl, 2,6-pyridyl, 2,5-furanyl or phenyl unsubstituted or substituted with NH$_2$ or 2-chloro, and when R$_3$ and R$_3$' are hydrogen, then Ar$_1$ and Ar$_2$ are not both quinoline which is unsubstituted or substituted with C1–C4 alkyl.

24. The composition according to claim 23 which further comprises an anticancer agent.

25. The composition according to claim 24 wherein the anticancer agent is chosen from alkylating agents, platinum derivatives, antibiotic agents, antimicrotubule agents, anthracyclines, group I and II topoisomerases, fluoropyrimidines, cytidine analogues, adenosine analogues, L-asparaginase, hydroxyurea, trans-retinoic acid, suramine, irinotecan, topotecan, dexrazoxane, amifostine, heroeptin, oestrogenic and androgenic hormones and antivascular agents.

26. The composition according to claim 23 used in conjunction with radiation treatment.

27. The composition according to claim 24 wherein each of the components is administered simultaneously, separately or sequentially.

28. The composition according to claim 26 wherein the compound and the radiation treatment are administered simultaneously, separately or sequentially.

29. A method of treatment of a cancer in a patient comprising administering to said patient a therapeutically effective amount of a compound of formula (I):

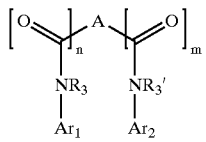

(I)

wherein
n and m are 1;
A represents:
a 5- to 6-membered heterocyclic radical containing a sulfur, oxygen or nitrogen atom;
a pheny; or
a diazine group; and wherein
the heterocyclic, phenyl and diazine are optionally substituted with one or more radicals chosen from halogen, C1–C4 alkyl, and thio, oxy or amino which are themselves optionally substituted with one or more C1–C4 alkyl;

R$_3$ and R'$_3$, which are identical or different, represent independently of each other hydrogen or C1–C4 alkyl;

Ar$_1$ and Ar$_2$, which are identical or different, and are independently of each other selected from:
a quinoilne optionally substituted with at least
a group N(Ra)(Rb) in which Ra and Rb are identical or different, and are independently of each other hydrogen or a C1–C4 alkyl; or
a C1–C4 alkyl or alkoxy;
a quinoline possessing a nitrogen atom in quaternary form;
a pyridine optionally attached at the 4-position or fused with an aryl or heteroaryl group, optionally substituted with a C1–C4 alkyl; or
a phenyl optionally substituted with halogen, C1–C4 alkoxy, cyano, carbonylamino optionally substituted with one or more C1–C4 alkyl, guanyl, C1–C4 alkylthio, amino, C1–C4 alkylamino, C1–C4 dialkylamino, nitro, C1–C4 alkyleneamino or C2–C4 alkenyleneamino;

or an isomer, an enantiomer, a diastereoisomer or a mixture thereof, or a pharmaceutically acceptable salt thereof:
with the proviso that:
when A is 2,5-pyridyl, 2,6-pyridyl, 2,5-furanyl or phenyl unsubstituted or substituted with NH$_2$ or 2-chloro, and when R$_3$ and R$_3$' are hydrogen, then Ar$_1$ and Ar$_2$ are not both quinoline which is unsubstituted or substituted with C1–C4 alkyl.

* * * * *